US011172864B2

(12) United States Patent
Parker et al.

(10) Patent No.: US 11,172,864 B2
(45) Date of Patent: Nov. 16, 2021

(54) MONITORING BRAIN NEURAL POTENTIALS

(71) Applicant: Closed Loop Medical Pty Ltd, Artarmon (AU)

(72) Inventors: John Louis Parker, Artarmon (AU); Gerrit Eduard Gmel, Artarmon (AU)

(73) Assignee: Closed Loop Medical Pty Ltd, Artarmon (AU)

(*) Notice: Subject to any disclaimer, the term of this patent is extended or adjusted under 35 U.S.C. 154(b) by 0 days.

(21) Appl. No.: 15/036,395

(22) PCT Filed: Nov. 14, 2014

(86) PCT No.: PCT/AU2014/001049
§ 371 (c)(1),
(2) Date: May 12, 2016

(87) PCT Pub. No.: WO2015/070281
PCT Pub. Date: May 21, 2015

(65) Prior Publication Data
US 2016/0287126 A1    Oct. 6, 2016

(30) Foreign Application Priority Data

Nov. 15, 2013  (AU) ................................ 2013904434
Mar. 26, 2014  (AU) ................................ 2014901076
Oct. 24, 2014  (AU) ................................ 2014904271

(51) Int. Cl.
*A61B 5/377*    (2021.01)
*A61B 5/00*     (2006.01)
(Continued)

(52) U.S. Cl.
CPC .............. *A61B 5/377* (2021.01); *A61B 5/316* (2021.01); *A61B 5/4064* (2013.01);
(Continued)

(58) Field of Classification Search
CPC .............. A61N 1/36135; A61N 1/0529; A61N 1/0534; A61N 1/36132; A61N 1/36067;
(Continued)

(56) References Cited

U.S. PATENT DOCUMENTS 3,724,467 A   4/1973  Avery et al.
3,736,434 A   5/1973  Darrow
(Continued)

FOREIGN PATENT DOCUMENTS

AU    2013277009 B2    1/2016
CN      103648583 A    3/2014
(Continued)

OTHER PUBLICATIONS

Tarik Al-ani, Fanny Cazettes, Stéphane Palfi, Jean-Pascal Lefaucheur, Automatic removal of high-amplitude stimulus artefact from neuronal signal recorded in the subthalamic nucleus, In Journal of Neuroscience Methods, vol. 198, Issue 1, 2011, pp. 135-146, ISSN 0165-0270, https://doi.org/10.1016/j.jneumeth.2011.03.022.*
(Continued)

*Primary Examiner* — Christian Jang
*Assistant Examiner* — Karen E Toth
(74) *Attorney, Agent, or Firm* — KPPB LLP

(57) ABSTRACT

Neural activity in the brain arising from a stimulus is monitored. A stimulus is applied to a target structure of the brain and a neural measurement is obtained from at least one electrode implanted in contact with the target structure. The neural measurement is configured to capture a measure of any late response arising in the target structure, typically being a neural response arising after conclusion of an ECAP, such as in the period 1.5-10 ms after stimulus onset. The late response(s) can be a useful biomarker such as of therapeutic ranges of deep brain stimulation, disease progression, medication efficacy, and intra-operative changes.

20 Claims, 19 Drawing Sheets

(51) Int. Cl.
   *A61N 1/36* (2006.01)
   *A61B 5/316* (2021.01)
   *A61B 5/291* (2021.01)
(52) U.S. Cl.
   CPC .......... *A61B 5/4839* (2013.01); *A61B 5/4848* (2013.01); *A61B 5/6868* (2013.01); *A61N 1/36067* (2013.01); *A61N 1/36139* (2013.01); *A61B 5/291* (2021.01); *A61B 5/4076* (2013.01); *A61N 1/36175* (2013.01)
(58) Field of Classification Search
   CPC .. A61N 1/36139; A61N 1/36175; A61B 5/24; A61B 5/377; A61B 5/291; A61B 5/369; A61B 5/4064; A61B 5/7246; A61B 5/7282; A61B 5/316; A61B 5/4839; A61B 5/4848; A61B 5/6868; A61B 5/4076; G16H 20/40; G06K 9/00496; G06K 9/00523
   See application file for complete search history.

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | Van et al. |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | MacDonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De |
| 7,742,810 B2 | 6/2010 | Moffitt |
| 7,792,584 B2 | 9/2010 | Van et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,359,102 B2 | 1/2013 | Thacker et al. |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,588,929 B2 | 11/2013 | Davis et al. |
| 8,670,830 B2 | 3/2014 | Carlson et al. |
| 8,886,323 B2 | 11/2014 | Wu et al. |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Marcelo |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |

(56) References Cited

U.S. PATENT DOCUMENTS

| | | |
|---|---|---|
| 2005/0203600 A1 | 9/2005 | Wallace |
| 2005/0209655 A1 | 9/2005 | Bradley et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1* | 12/2008 | Cholette ............... A61N 1/0556 607/60 |
| 2008/0319508 A1 | 12/2008 | Botros et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1* | 8/2010 | Lozano ............... A61B 5/04001 607/45 |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1* | 2/2011 | Chian ................. A61B 5/04001 600/554 |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1* | 9/2014 | Papay .................. A61B 5/0484 600/554 |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1* | 11/2014 | Grill ........................ A61B 5/24 607/45 |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0126839 A1 | 5/2015 | Li et al. |
| 2015/0148869 A1 | 5/2015 | Dorvall, II et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |
| 2016/0082268 A1 | 3/2016 | Hershey et al. |
| 2016/0101289 A1 | 4/2016 | Stolen et al. |
| 2016/0106980 A1 | 4/2016 | Sürth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1 | 6/2016 | Min et al. |

(56) References Cited

U.S. PATENT DOCUMENTS

| | | |
|---|---|---|
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0030339 A1 | 1/2019 | Baru et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0016091 A1 | 1/2021 | Parker et al. |
| 2021/0121696 A1 | 4/2021 | Parker et al. |
| 2021/0162214 A1 | 6/2021 | Parker |

FOREIGN PATENT DOCUMENTS

| | | | |
|---|---|---|---|
| CN | 103654762 A | 3/2014 | |
| CN | 103842022 A | 6/2014 | |
| CN | 104411360 A | 3/2015 | |
| EP | 0219084 | 4/1987 | |
| EP | 1244496 A1 | 10/2002 | |
| EP | 0998958 B1 | 8/2005 | |
| EP | 2019716 A | 11/2007 | |
| EP | 2243510 A2 | 10/2010 | |
| EP | 2443995 A2 | 4/2012 | |
| EP | 2520327 A2 | 11/2012 | |
| EP | 2707095 A1 | 3/2014 | |
| EP | 3229893 A1 | 10/2017 | |
| JP | 2006504494 A | 2/2006 | |
| JP | 2009512505 A | 3/2009 | |
| JP | 2012524629 | 10/2012 | |
| JP | 2013500779 A | 1/2013 | |
| JP | 2013527784 A | 7/2013 | |
| JP | 2013536044 A | 9/2013 | |
| JP | 2014522261 A | 9/2014 | |
| JP | 2014523261 A | 9/2014 | |
| WO | 1983003191 A | 9/1983 | |
| WO | 1993001863 A1 | 2/1993 | |
| WO | 9612383 A1 | 4/1996 | |
| WO | 2000002623 A1 | 1/2000 | |
| WO | 2002036003 A1 | 11/2001 | |
| WO | 2002038031 | 5/2002 | |
| WO | 2002049500 A2 | 6/2002 | |
| WO | 2002082982 A1 | 10/2002 | |
| WO | 2003028521 A2 | 4/2003 | |
| WO | 2003043690 | 5/2003 | |
| WO | 2003103484 | 12/2003 | |
| WO | 2004021885 A1 | 3/2004 | |
| WO | 2004103455 | 12/2004 | |
| WO | 2005032656 A1 | 4/2005 | |
| WO | 2005105202 A1 | 11/2005 | |
| WO | 2005122887 A2 | 12/2005 | |
| WO | 2006091636 A2 | 8/2006 | |
| WO | 2007050657 A1 | 5/2007 | |
| WO | 2007064936 A1 | 6/2007 | |
| WO | 2007127926 A2 | 11/2007 | |
| WO | 2007130170 A1 | 11/2007 | |
| WO | 2008004204 A1 | 1/2008 | |
| WO | 2008049199 A1 | 5/2008 | |
| WO | 2009002072 A2 | 12/2008 | |
| WO | 2009002579 A1 | 12/2008 | |
| WO | 2009010870 A2 | 1/2009 | |
| WO | 2009130515 A2 | 10/2009 | |
| WO | 2009146427 A1 | 12/2009 | |
| WO | 2010013170 A1 | 2/2010 | |
| WO | 2010044989 A2 | 4/2010 | |
| WO | 2010051392 A1 | 5/2010 | |
| WO | 2010051406 A1 | 5/2010 | |
| WO | 2010057046 A2 | 5/2010 | |
| WO | 2010124139 A1 | 10/2010 | |
| WO | 2010138915 A1 | 12/2010 | |
| WO | 2011011327 A1 | 1/2011 | |
| WO | 2011014570 A1 | 2/2011 | |
| WO | 2011066477 A1 | 6/2011 | |
| WO | 2011066478 A1 | 6/2011 | |
| WO | 2011112843 A1 | 9/2011 | |
| WO | 2011119251 A2 | 9/2011 | |
| WO | 2011159545 A2 | 12/2011 | |
| WO | 2012027252 A2 | 3/2012 | |
| WO | 2012027791 A1 | 3/2012 | |
| WO | 2012155183 A1 | 11/2012 | |
| WO | 2012155184 A1 | 11/2012 | |
| WO | 2012155185 A1 | 11/2012 | |
| WO | 2012155187 A1 | 11/2012 | |
| WO | 2012155188 A1 | 11/2012 | |
| WO | 2012155189 A1 | 11/2012 | |
| WO | 2012155190 A1 | 11/2012 | |
| WO | 2012162349 A1 | 11/2012 | |
| WO | WO 2012/155188 * | 11/2012 | ............... A61N 1/05 |
| WO | 2013063111 A1 | 5/2013 | |
| WO | 2013075171 A1 | 5/2013 | |
| WO | 2014071445 A1 | 5/2014 | |
| WO | 2014071446 A1 | 5/2014 | |
| WO | 2014143577 A1 | 9/2014 | |
| WO | 2014150001 A1 | 9/2014 | |
| WO | 2015070281 A1 | 5/2015 | |
| WO | 2015074121 A1 | 5/2015 | |
| WO | 2015109239 A1 | 7/2015 | |
| WO | 2015143509 A1 | 10/2015 | |
| WO | 2015168735 A1 | 11/2015 | |
| WO | 2016011512 | 1/2016 | |
| WO | 2016048974 A1 | 3/2016 | |
| WO | 2016059556 A1 | 4/2016 | |
| WO | 2016077882 A1 | 5/2016 | |
| WO | 2016090420 A1 | 6/2016 | |
| WO | 2016090436 A1 | 6/2016 | |
| WO | 2016115596 A1 | 7/2016 | |
| WO | 2016161484 A2 | 10/2016 | |
| WO | 2016168798 A1 | 10/2016 | |
| WO | 2016191807 A1 | 12/2016 | |
| WO | 2016191808 A1 | 12/2016 | |
| WO | 2016191815 A1 | 12/2016 | |
| WO | 2017173493 A1 | 10/2017 | |
| WO | 2017210352 A1 | 12/2017 | |
| WO | 2017219096 A1 | 12/2017 | |
| WO | 2018119220 A1 | 6/2018 | |
| WO | 2018160992 A1 | 9/2018 | |
| WO | 2019178634 A1 | 9/2019 | |
| WO | 2019204884 A1 | 10/2019 | |
| WO | 2019231796 A1 | 12/2019 | |
| WO | 2020082118 A1 | 4/2020 | |
| WO | 2020082126 A1 | 4/2020 | |
| WO | 2020082128 A1 | 4/2020 | |

(56) References Cited

FOREIGN PATENT DOCUMENTS

| WO | 2020087123 A1 | 5/2020 |
| WO | 2020087135 A1 | 5/2020 |

OTHER PUBLICATIONS

International Preliminary Report on Patentability for International Application No. PCT/AU2015/050753, Report dated Jun. 13, 2017, 7 pgs.
International Search Report and Written Opinion for International Application No. PCT/AU2016/050263, completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
Alam et al., "Evaluation of optimal electrode configurations for epidural spinal cord stimulation in cervical spinal cord injured rats", Journal of Neuroscience Methods, Mar. 2015, 28 pgs.
Fisher, "F-Waves—Physiology and Clinical Uses", The Scientific World Journal, (2007) 7, pp. 144-160.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Yamada et al., "Extraction and Analysis of the Single Motor Unit F-Wave of the Median Nerve", EMG Methods for Evaluating Muscle and Nerve Function, InTech, 2012, 15 pgs.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
Extended European Search Report for EP Application 12785483.4 completed Sep. 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 09 Pgs.
Extended European Search Report for European Application No. 14861553.7, Search completed Jun. 8, 2017, dated Jun. 19, 2017, 8 Pgs.
Extended European Search Report for European Application No. 14863597.2, Search completed Jun. 6, 2017, dated Jun. 13, 2017, 9 Pgs.
Extended European Search Report for European Application No. 13853514.1, Search completed Jun. 8, 2016, dated Jun. 15, 2016, 07 Pgs.
International Preliminary Report on Patentability for International Application No. PCT/AU2012/001441, Report dated May 27, 2014, 10 pgs.
International Search Report & Written Opinion for International Application No. PCT/AU2013/001280, Search Completed Jan. 16, 2014, dated Jan. 16, 2014, 8 Pgs.
International Search Report & Written Opinion for International Application PCT/AU2013/001279, Search Completed Jan. 9, 2014, dated Jan. 9, 2014, 9 Pgs.
International Search Report and Written Opinion for International Application No. PCT/AU2011/001127, date completed Nov. 11, 2011, dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/050369, Search completed Feb. 20, 2015, dated Feb. 20, 2015, 14 Pgs.
International Search Report and Written Opinion for International Application No. PCT/AU2015/050135, Search completed Jun. 30, 2015, dated Jun. 30, 2015, 26 Pgs.
International Search Report and Written Opinion for International Application No. PCT/AU2015/050422, Search completed Oct. 14, 2015, dated Oct. 14, 2015, 17 Pgs.
International Search Report and Written Opinion for International Application No. PCT/AU2015/050724, Search completed May 9, 2016, dated May 9, 2016, 8 Pgs.
International Search Report and Written Opinion for International Application No. PCT/AU2015/050753, Search completed Feb. 10, 2016, dated Feb. 10, 2016, 10 Pgs.
International Search Report and Written Opinion for International Application No. PCT/AU2015/050787, Search completed Mar. 16, 2016, dated Mar. 16, 2016, 10 Pgs.
International Search Report and Written Opinion for International Application No. PCT/AU2016/050019, Search completed May 4, 2016, dated May 4, 2016, 16 Pgs.
International Search Report and Written Opinion for International Application No. PCT/AU2015/050215, Search completed Jul. 30, 2015, dated Jul. 30, 2015, 8 Pgs.
International Search Report for Australian Application 2011901829 Search Completed Feb. 6, 2012, dated Feb. 7, 2012, 3pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 10 pgs.

(56) References Cited

OTHER PUBLICATIONS

Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm,, Capture Date Jul. 9, 2012, Printed on May 11, 2017.
"Advanced Pain Therapy using Neurostimulation for Chronic Pain", Medtronic RestoreSensor clinical trial paper, Clinical summary, Nov. 2011, pp. 32.
"Battelle Neurotechnology—Moving Beyond the Limits in Neurotechnology", Battelle, www.battelle.org, May 2014, pp. 1-2.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Andreassen, S. et al., "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Balzer et al., "Localization of cervical and cervicomedullary stimulation leads for pain treatment using median nerve somatosensay evoked potential collision testing", Journal of Neurosurgery, Jan. 2011, vol. 114, No. 1 : pp. 200-205.
Blum, A. R., "An Electronic System for Extracelluar Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.
Brown et al., "Impact of Deep Brain Stimulation on Upper Limb Askinesia in Parkingson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. Vol. 6. IEEE, 1992. pp. 2600-2601.
Coquery et al., "Backward and forward masking in the perception of cutaneous stimuli", Perception & Psychophysics, 1973, vol. 13.No. 2, pp. 161-163.
Dawson, G. D., "The relative excitability and conduction velocity of sensory and motor nerve fibres in man", Journal of Physiology, 1956, vol. 131(2), pp. 436-451.
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL., 4 pgs.

Dillier, N et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
Fagius, J. et al., "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Franke et al., Felix , "An Online Spike Detection and Spike Classification Algorithm Capable of Instantaneous Resolution of Overlapping Spikes", Journal of Computational Neuroscience, 2010, vol. 29, No. 1-2, pp. 127-148.
Fuentes et al., "Spinal Cord Stimulation Restores Locomotion in Animal Models of Parkinson's Disease", Science, vol. 323, No. 5921, Mar. 20, 2009, pp. 1578-1582.
George et al., "Vagus nerve stimulation: a new tool for brain research and therapy", Biological Psychiatry 47, No. 4, Feb. 15, 2000, pp. 287-295.
Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.
Gorman et al., "ECAP Mapping of the Spinal Cord: Influence of Electrode Position on Aβ Recruitment", (2012).,In 16th Annual Meeting. Presented at the North American Neuromodulation Society, Las Vegas, NV.
Gorman et al., "Neural Recordings For Feedback Control Of Spinal Cord Stimulation: Reduction Of Paresthesia Variability.", 2013,In International Neuromodulation Society 11th World Congress. Presented at the International Neuromodulation Society 11th World Congress, Berlin, Germany.
Hallstrom et al, "Distribution of lumbar spinal evoked potentials and their correlation with stimulation-induced paresthesiae", (1991),Electroencephalography and clinical neurophysiology 80:126-139.
Harper, A. A. et al., "Conduction Velocity is Related to Morphological Cell Type in Rat Dorsal Root Ganglion Neurones", J. Physiol, (1985), 359, pp. 31-46.
Holsheimer et al., "Optimum Electrode Geometry for Spinal Cord Stimulation: the Narrow Bipole and Tripole", Medical and Biological Engineering and Computing, 35, No. 5, 1997, pp. 493-497.
Huff, Terry B. et al., "Real-Time CARS Imaging Reveals a Calpain-Dependent Pathway for Paranodal Myelin Retraction during High-Frequency Stimulation", PLoS ONE vol. 6, issue 3 (Mar. 3, 2011): e17176, 11 pgs.
Kent et al., "Instrumentation to Record Evoked Potentials for Closed-Loop Control of Deep Brain Stimulation", Conf. Proc. IEEE Eng. Med Biol. Sol, Aug. 2012, 10 pgs.
Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.
Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi: 10.1016/50306-4522(98)00022-0.
Krames et al., "Neuromodulation", 1st Edition, Academic Press, 2009, p. 540-541.
Krarup, Christian, "Compound sensory action potential in normal and pathological human nerves", Muscle & nerve, vol. 29, No. 4 (2004), pp. 465-483.
Krishnan et al., "Excitability Differences in Lower-Limb Motor Axons During and After Ischemia", Muscle & nerve, vol. 31, No. 2 (2005), pp. 205-213.

(56) References Cited

OTHER PUBLICATIONS

Kumar et al., "Deep Brain Stimulation for Intractable Pain: a 15-year Experience", Neurosurgery, Issue 40, No. 4, Apr. 1997, pp. 736-747.
Kumar et al., "Double-blind evaluation of subthalamic nucleus deep brain stimulation in advanced Parkinson's disease", by the American Academy of Neurology, 51, No. 3, Sep. 1, 1998, pp. 850-855.
Kumar et al., "Globus Pallidus Deep Brain Stimulation for Generalized Dystonia: Clinical and PET Investigation", Neurology, 53, No. 4, 1999, pp. 871-874.
Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.
Lempka, Scott, "The Electrode-Tissue Interface During Recording and Stimulation in the Central Nervous System", published on May 2010.
Levy et al., "Incidence and Avoidance of Neurologic Complications with Paddle Type Spinal Cord Stimulation Leads", Neuromodulation 14(15), Sep. 2011, pp. 412-422.
Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Mahnam, A et al., "Measurement of the current-distance relationship using a novel refractory interaction technique", J. Neural Eng. 6(2): 036005, published May 20, 2009.
Markandey Vishal, "ECG Implementation on the TMS320C5515 DSP Medical Development Kit (MDK)", Texas Instruments Application Report Jun. 2010, 35 pgs.
Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.
Matzner et al., "Na+ Conductance and the Threshold for Repetitive Neuronal Firing", Brain Research 597, No. 1 (Nov. 27, 1992): 92-98, doi: 10.1016/0006-8993(92)91509-D.
McGill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.
Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi: 10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.

Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik, Kristin et al., "Pathological C-fibres in patients with a chronic painful condition", Brain (2003), 126, 567-578.
Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.
Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.
Parker et al., "Compound action potentials recorded in the human spinal cord during neurostimulation for pain relief", Pain, 2012, vol. 153, pp. 593-601.
Parker et al., "Electrically Evoked Compound Action Potentials Recorded From the Sheep Spinal Cord", Neuromodulation, vol. 16, 2013, pp. 295-303.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ridder et al., "Burst Spinal Cord Stimulation toward Paresthesia-Free Pain Suppression", May 2010, vol. 66, pp. 986-990.
Roy, S. H. et al., "Effects of Electrode Location on Myoelectric Conduction Velocity and Median Frequency Estimates", J. Appl. Physiol. 61 (4), 1986, pp. 1510-1517.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S, "Electrode/Electrolyte Interfaces: Structure and Kinetics of Charge Transfer", Fuel Cells, 2006, Chapter 2, 67 Pages.
Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", Spine, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tscherter et al., "Spatiotemporal Characterization of Rhythmic Activity in Rat Spinal Cord Slice Cultures", European Journal of Neuroscience 14, No. 2 (2001), pp. 179-190.

(56) References Cited

OTHER PUBLICATIONS

Van Den Berg et al., "Nerve fiber size-related block of action currents by phenytoin in mammalian nerve", Epilepsia, Nov. 1994, 35(6), pp. 1279-1288.
Villavicencio, Alan T. "Laminectomy versus Percutaneous Electrode Placement for Spinal Cord Stimulation," Neurosurgery, vol. 46 (2), Feb. 2000, pp. 399-405.
Vleggeert et al., Lankamp, "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi: 10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yearwood, T. L., "Pulse Width Programming in Spinal Cord Stimulation: a Clinical Study", Pain Physician. 2010. vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan, S. et al., "Recording monophasic action potentials using a platinum-electrode ablation catheter", Europace. Oct. 2000; 2(4):312-319.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Type Search Report for International Application No. AU 2015902393, Search completed May 16, 2016, dated May 16, 2016, 8 Pgs.
International Search Report and Written Opinion for International Application No. PCT/AU2014/001049, Search completed Feb. 10, 2015, dated Feb. 10, 2015, 8 Pgs.
Devergnas, A. et al., "Cortical potentials evoked by deep brain stimulation in the subthalamic area", Frontiers in Systems Neuroscience, vol. 5, Article 30, May 13, 2011. doi:10.3389/fnsys.2011.00030.
Kent, A. R. et al., "Recording evoked potentials during deep brain stimulation: development and validation of instrumentation to suppress the stimulus artefact", J Neural Eng., Jun. 2012, vol. 9(3):036004, doi: 10.1088/1741-2560/9/3/036004.
Li, S. et al., "Resonant antidromic cortical circuit activation as a consequence of high-frequency subthalamic deep-brain stimulation", J Neurophysiol., vol. 98(6):3525-37, Oct. 10, 2007, doi:10.1152/jn.00808.2007, pp. 3526-3532.
European Search Report for European Application No. 15861444.6, Search completed Jul. 13, 2018, dated Jul. 23, 2018, 8 pgs.
Extended European Search Report for European Application No. 16739680.3, Search completed Jun. 1, 2018, dated Jun. 12, 2018, 9 pgs.
International Search Report and Written Opinion for International Application No. PCT/AU2017/050296, Search completed Jul. 28, 2017, dated Jul. 28, 2017, 10 pgs.
French et al., "Information transmission at 500 bits/s by action potentials in a mechanosensory neuron of the cockroach", Neuroscience Letters, vol. 243, No. 1-3, Feb. 1, 1998, pp. 113-116.
He et al., "Perception threshold and electrode position for spinal cord stimulation", Pain, 59 (1994) 55-63 pages.
Herreras, "Local Field Potentials: Myths and Misunderstandings", Frontiers in Neural Circuits, Dec. 15, 2016, vol. 10, Article 1101, 16 pgs.
Holsheimer et al., "Significance of the Spinal Cord Position in Spinal Cord Stimulation", Acta Neurochir (1995) [Suppl] 64: 119-124 pages.
Holsheimer et al., "Spinal Geometry and Paresthesia Coverage in Spinal Cord Stimulation", (1998 paper) 8 pages.
Olin et al., "Postural Changes in Spinal Cord Stimulation Perceptual Thresholds", Neuromodulation, vol. 1, No. 4, 1998, pp. 171-175.
Rattay, "Analysis of Models for External Stimulation of Axons", IEEE Transactions on Biomedical Engineering, vol. BME-33, No. 10, Oct. 1986, pp. 974-977.
Ross et al., "Improving Patient Experience with Spinal Cord Stimulation: Implications of Position-Related Changes in Neurostimula-

(56) References Cited

OTHER PUBLICATIONS tion", Neuromodulation 2011; e-pub ahead of print. DOI: 10.1111/j.1525-1403.2011.00407.x 6 pages.

Struijk, "The Extracellular Potential of a Myelinated Nerve Fiber in an Unbounded Medium and in Nerve Cuff Models", Biophysical Journal vol. 72 Jun. 1997 2457-2469.

Extended European Search Report for European Application No. 15768956.3, Search completed Oct. 3, 2017, dated Oct. 10, 2017, 8 Pgs.

Extended European Search Report for European Application No. 16802237.4, Search completed Dec. 11, 2018, dated Dec. 19, 2018, 9 Pgs.

Extended European Search Report for European Application No. 16802238.2, Search completed Oct. 17, 2018, dated Oct. 24, 2018, 8 Pgs.

International Preliminary Report for International Application No. PCT/AU2017/050296, dated Oct. 9, 2018, 7 Pgs.

International Preliminary Report for International Application No. PCT/AU2017/050647, dated Dec. 25, 2018, 8 pgs.

International Search Report and Written Opinion for International Application No. PCT/AU2017/050647, Search completed Sep. 29, 2017, dated Sep. 29, 2017, 13 Pgs.

Partial European Search Report for European Application No. 16775966.1, Search completed Oct. 26, 2018, dated Nov. 6, 2018, 11 Pgs.

Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.

Bahmer et al., "Effects of electrical pulse polarity shape on intra cochlear neural responses in humans: Triphasic pulses with cathodic second phase", Hearing Research, 2013, vol. 306, pp. 123-130.

Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.

Jeffrey et al., "A reliable method for intracranial electrode implantation and chronic electrical stimulation in the mouse brain", BMC Neuroscience. Biomed Central. London. GB. vol. 14. No. 1. Aug. 6, 2013, p. 82.

Tronnier et al., "Magnetic Resonance Imaging with Implanted Neurostimulators: An In Vitro and In Vivo Study", Jan. 1999, Neurosurgery, vol. 44(1), p. 118-125 (Year: 1999).

Extended European Search Report for European Application No. 17778477.4, report completed Nov. 12, 2019, dated Nov. 20, 2019, 7 pgs.

Extended European Search Report for European Application No. 17814341.8, report completed Dec. 12, 2019, report dated Jan. 2, 2020, 8 pgs.

Japanese Office Action for Application No. 2017-546830, dated Feb. 20, 2020, 5 pages with English translation.

Japanese Office Action for Application No. 2017-553090, dated Mar. 16, 2020, 12 pages with English translation.

Japanese Office Action for Application No. 2018-513699, dated Jun. 8, 2020, 7 pages with English translation.

Office Action for Chinese Patent Application No. 201680020725.4, dated Mar. 16, 2020, 8 pgs.

Kent, "Characterization of Evoked Potentials During Deep Brain Stimulation in the Thalamus", Dissertation, Duke University. Retrieved from https://hdl.handle.net/10161/8195, 2013.

Extended European Search Report for European Application No. 15789515.2, Search completed Dec. 4, 2017, dated Jan. 30, 2018, 7 Pgs.

International Preliminary Report on Patentability for International Application No. PCT/AU2018/050278, dated Sep. 29, 2020, 7 pgs.

International Preliminary Report on Patentability for International Application No. PCT/AU2019/050384, dated Oct. 27, 2020, 8 pgs.

International Search Report and Written Opinion for International Application No. PCT/AU2018/050278, Search completed Jun. 18, 2018, dated Jun. 18, 2018, 12 Pgs.

International Search Report and Written Opinion for International Application No. PCT/AU2019/050384, Search completed Jun. 25, 2019, dated Jun. 25, 2019, 15 Pgs.

Kopelman et al., "Attempted Reversible Sympathetic Ganglion Block by an Implantable Neurostimulator", Interactive CardioVascular and Thoracic Surgery, Feb. 7, 2012, vol. 14, Issue 5, pp. 605-609, doi:10.1093/icvts/ivr137.

Australian Examination Report for Application No. 2019283936, dated Apr. 1, 2021, 7 pages.

International Search Report for International Application No. PCT/AU2019/051151, International Filing Date Oct. 22, 2019, Search Completed Feb. 24, 2020, dated Feb. 24, 2020, 9 pgs.

International Search Report for International Application No. PCT/AU2019/051160, International Filing Date Oct. 23, 2019, Search Completed Jan. 28, 2020, dated Jan. 28, 2020, 13 pgs.

International Search Report for International Application No. PCT/AU2019/051163, International Filing Date Oct. 23, 2019, Search Completed Jan. 21, 2020, dated Jan. 31, 2020, 8 pgs.

International Search Report for International Application No. PCT/AU2019/051197, International Filing Date Oct. 30, 2019, Search Completed Jan. 21, 2020, dated Jan. 21, 2020, 15 pgs.

International Search Report for International Application No. PCT/AU2019/051210, International Filing Date Nov. 2, 2019, Search Completed Feb. 4, 2020, dated Feb. 4, 2020, 10 pgs.

Japanese Office Action for Application No. 2018-552138, dated Mar. 1, 2021, 7 pages with English translation.

"Evoke 12C Percutaneous Leads", Saluda Medical, specifications available in the "Evoke Surgical Guide", version 6, http://www.saludamedical.com/manuals/, retrieved May 2017.

Bratta et al., "Orderly Stimulation of Skeletal Muscle Motor Units with Tripolar Nerve Cuff Electrode", IEEE Transactions on Biomedical Engineering, vol. 36, No. 8, 1989.

Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi:10.1111/j.1526-4637.2009.00632.X.

Cong et al., "A 32-channel modular bi-directional neural interface system with embedded DSP for closed-loop operation", 40th European Solid State Circuits Conference (ESSCIRC), 2014, pp. 99-102.

Connolly et al., "Towards a platform for prototyping control systems for optimization of neuromodulation therapies", IEEE Biomedical Circuits and Systems Conference (BioCAS), 2015, pp. 1-4.

Delgado et al., "Measurement and interpretation of electrokinetic phenomena", Pure Appl. Chem., 2005, vol. 77, No. 10, pp. 1753-1805.

Fitzpatrick et al., "A Nerve Cuff Design for the Selective Activation and Blocking of Myelinated Nerve Fibers", IEEE Engineering in Medicine and Biology Society, vol. 13, No. 2, 1991.

Howell et al., "Evaluation of Intradural Stimulation Efficiency and Selectivity in a Computational Model of Spinal Cord Stimulation", Plos One, DOI:10.1371/journal.pone.0114938, Dec. 23, 2014.

Jones et al., "Scaling of Electrode-Electrolyte Interface Model Parameters in Phosphate Buffered Saline", IEEE Transactions on Biomedical Circuits and Systems, 2015, vol. 9, No. 3, pp. 441-448.

North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.

Peterson et al., "Stimulation artifact rejection in closed-loop, distributed neural interfaces", ESSCIRC, 42nd European Solid-State Circuits Conference, Lausanne, 2016, pp. 233-235.

Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994.

Rijkhoff et al., "Orderly Recruitment of Motoneurons in an Acute Rabbit Model", Annual International Conference of the IEEE Engineering in Medicine and Biology Society, vol. 20, No. 5, 1998.

(56) References Cited

OTHER PUBLICATIONS

Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.

\* cited by examiner

MONITORING BRAIN NEURAL POTENTIALS

CROSS-REFERENCE TO RELATED APPLICATIONS

This application is a national stage of Application No. PCT/AU2014/001049 filed Nov. 14, 2014, which application claims the benefit of Australian Provisional Patent Application No. 2013904434 filed Nov. 15, 2013, Australian Provisional Patent Application No. 2014901076 filed Mar. 26, 2014, and Australian Provisional Patent Application No. 2014904271 filed Oct. 24, 2014, the disclosures of which are incorporated herein by reference in their entirety.

TECHNICAL FIELD

The present invention relates to neural modulation in the brain, and in particular relates to a method for monitoring neural measurements of activity in the brain arising from stimulation in order to monitor therapeutic effect of the stimulation, or to monitor therapeutic effect of medicine, or to monitor disease state.

BACKGROUND OF THE INVENTION

Neuromodulation involves applying an electric stimulus to biological tissue in order to produce a therapeutic effect. Neuromodulation can be non-invasive such as by transcutaneous electrical nerve stimulation (TENS), transcranial magnetic stimulation (TMS), or highly invasive when requiring the implantation of one or more electrodes and a controlling stimulator as in the case of deep brain stimulation (DBS). DBS has become the most effective treatment for late stage Parkinson's disease, but is a highly invasive therapy requiring the implantations of two leads deep into subcortical nuclei and connection to one or more pulse generators implanted in the chest. Many DBS electrode target structures have been studied to treat a wide variety of diseases and the preferred location of the electrode varies depending on the disease that is being treated. In the case of Parkinson's disease, the preferred targets are the internal segment of the globus pallidus (GPi) and the subthalamic nucleus (STN). The GPi has also been targeted for Huntington's disease and Tourette's syndrome, the nucleus accumbens has been targeted for chronic depression and alcohol dependence, and the fornix is being trialed for Alzheimer's disease.

Parkinson's disease is a degenerative disorder affecting dopamine-releasing cells in the substantia nigra. Many theories describing the functioning of the basal ganglia and how this degeneration relates to Parkinson's disease have been proposed, however all such theories have significant inadequacies in describing all aspects of Parkinson's disease, and understanding the mechanisms of DBS remains the focus of considerable research effort.

A significant reason for the lack of understanding about the mechanisms of DBS and the basal ganglia is the difficulty of measuring the direct responses of the nervous tissue to stimulation. Most of the findings are based on single-cell measurements on efferent structures and, until recently, it was impossible to adequately measure the direct compound response of the target structures because when recording close to the stimulation site, large artefacts (electrical and electrode artefacts) tend to mask the tissue response.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method of monitoring neural activity in the brain arising from a stimulus, the method comprising:

applying a stimulus to a target structure of the brain; and obtaining a neural measurement from at least one electrode implanted in contact with the target structure, the neural measurement configured to capture a measure of any late response arising in the target structure.

According to a second aspect the present invention provides an implantable device for monitoring neural activity in the brain arising from a stimulus, the device comprising:

a stimulus source for providing a stimulus to be delivered from one or more stimulus electrodes to a target structure of the brain; and measurement circuitry for obtaining a neural measurement from a sense electrode in contact with the target structure, the neural measurement configured to capture a measure of any late response arising in the target structure.

The measure of the late response in some embodiments comprises a record of substantially the entire duration of the late response. In the case of the subthalamic nucleus the measure of the late response in some embodiments may encompass a time period beginning 1-5 ms after the stimulus onset, more preferably beginning 1.5-4 ms after the stimulus onset, more preferably beginning 2-3 ms after the stimulus. In the case of the subthalamic nucleus the measure of the late response in some embodiments may encompass a time period ending 5-10 ms after the stimulus, more preferably ending 5.5-8 ms after the stimulus, more preferably ending 6.5-7.5 ms after the stimulus onset. It is to be noted that the late response as referred to herein may comprise multiple neural responses, so that the measure of the late response may comprise multiple maxima and minima.

The neural measurement in some embodiments is configured to also capture a measure of any compound action potential (CAP) arising directly from the stimulus, prior to the late response. In such embodiments a period encompassing the late response may be defined by reference to one or more features of the CAP, such as the CAP P2 peak, rather than defining such period relative to the stimulus.

The neural measurement is preferably obtained in accordance with the teaching of International Patent Publication No. WO2012/155183 by the present applicant, the content of which is incorporated herein by reference.

According to another aspect, the present invention provides a non-transitory computer readable medium for monitoring neural activity in the brain arising from a stimulus, comprising instructions which, when executed by one or more processors, causes performance of the following:

applying a stimulus to a target structure of the brain; and obtaining a neural measurement from at least one electrode implanted in contact with the target structure, the neural measurement configured to capture a measure of any late response arising in the target structure.

By capturing a measure of any late response arising in the target structure some embodiments of the present invention may deliver a diagnostic method. The presence, amplitude, morphology, and/or latency of the late response may be compared to healthy ranges and/or monitored for changes over time in order to diagnose a disease state. The method of the invention may be applied in some embodiments in order to determine a therapeutic effect of the stimulation, determine a therapeutic effect of medicine, and/or to monitor disease state. A therapeutic response may subsequently be ordered, requested and/or administered based on the diagnosis.

Some embodiments of the present invention may be applied specifically in relation to stimulation of the subthalamic nucleus. However alternative embodiments may be applied in relation to the application of stimuli to other portions of the brain in which an early neural response arises in a linear manner in response to the stimulus, and in which a non-linear late response subsequently arises which may be separately monitored to the early response.

The therapeutic effect determined from the late response may be used in some embodiments in order to regulate neural activity to a target level or target profile.

The therapeutic effect determined from the late response may be used in some other embodiments as an intraoperative tool to assist surgeons to implant an electrode at an ideal location or orientation. For example by exploring a stimulus parameter space repeatedly throughout implantation, while watching the late response, to find a location, orientation and stimulus paradigm which is therapeutic and of lowest power consumption, and/or to monitor for adverse side effects. In the case of epilepsy a neural region of heightened excitability, as indicated by early onset of the late response as compared to other regions, may be identified as a likely focus of focal seizures.

In still further embodiments, the late response may reveal an efficacy of a medication taken by the user, and may be used to adjust a stimulation paradigm over time as medicine wears off. Moreover, a reduction in efficacy of a medicine over time, or the monitoring of progression of a disease over time, such as over weeks, months or years, may be monitored by some embodiments of the present invention.

It is to be understood that the at least one electrode from which the neural measurement is obtained is implanted in electrical contact with the target structure but not necessarily in physical contact with the target structure. For example where the stimulus is applied to the STN, the at least one electrode from which the neural measurement is obtained may be implanted partly or wholly within the zona incerta or in another structure near the STN.

Some embodiments of the present invention may further provide for monitoring of local field periodic signals by reference to the late response. For example a peak-to-peak amplitude of the late response may be modulated by the heartbeat of the patient and thus the deep brain stimulator may in some embodiments be configured to monitor the patient's heart rate by reference to 0.5-3 Hz modulations of the peak to peak amplitude of a plurality of measurements of the late response, thus eliminating the need to provide a separate heart rate monitor, and without the need to interrupt the stimulation. These and/or other embodiments may further assess beta-band oscillations influencing the measurement(s) of the late response, which can be one of the main observable electrophysiological changes in PD.

BRIEF DESCRIPTION OF THE DRAWINGS

An example of the invention will now be described with reference to the accompanying drawings, in which.

DESCRIPTION OF THE PREFERRED EMBODIMENTS

The following describes a number of embodiments utilising measurement of the compound action potential arising from stimulation of the subthalamic nucleus (STN), and a number of applications that these measurements may have such as for improving the therapy. While the following embodiments relate to STN stimulation for Parkinson's disease, it is to be understood that other embodiments of the invention may be applied to other applications of deep brain stimulation.

Figure 1:
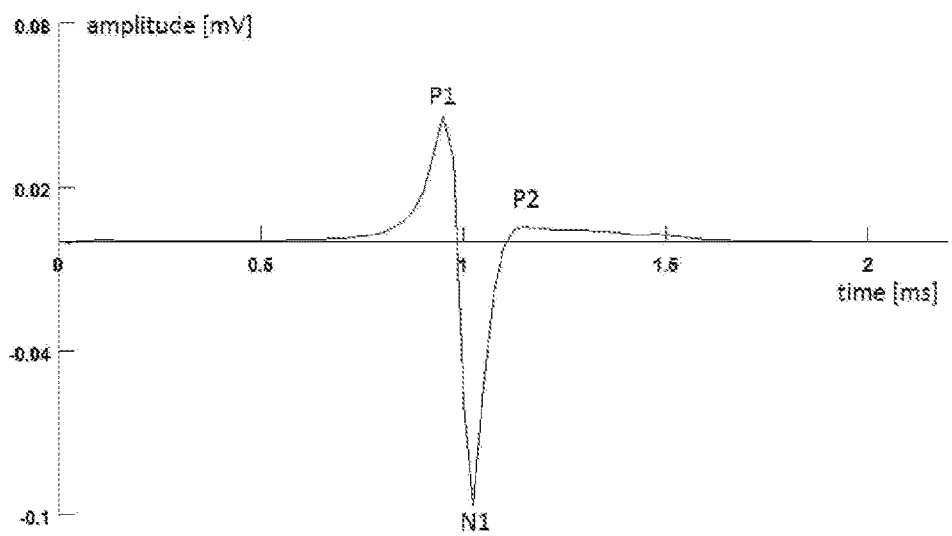
FIG. 1 illustrates a simulated single fibre action potential profile.

The combined response of nervous tissue to electrical stimulation usually takes the form of an evoked compound action potential (ECAP). For illustrative purposes, FIG. 1 shows the evoked action potential arising when simulating a single fibre from a spinal cord model. The three peaks characteristic of the action potential, respectively referred to as the P1, N1 and P2 peaks, are clearly visible. The typical response of multiple fibres together, namely the compound action potential (CAP), is usually smoother and more spread-out then the single fibre action potential profile shown in FIG. 1, but the 3 characteristic peaks are nevertheless still present in a CAP.

The details of the measurement technique used in the present embodiments are described in WO2012/155183, and its application in a feedback loop are described in WO2012/155188 by the present applicant, the content of which is incorporated herein by reference.

When seeking to measure neural responses arising from a stimulus in a target structure in the brain, as in the case of DBS, it is noted that this application necessitates very short distances between the stimulating site and the recording site, for example no more than about 5 to 9 millimetres for the STN, and in the present embodiment electrode 3 is positioned about 1.5 mm away from the stimulus site, this being the inter electrode spacing. Considering the propagation speed, and the necessity for a certain minimum blanking period during which the measurement amplifiers must be disconnected from the electrodes to avoid artefact, the ECAPs measured on electrodes at this range are truncated as seen in both plots of FIG. 2a in the period prior to about 1.2 ms after the initiation of the stimulus in both plots of FIG. 2 (note that the stimulus is not initiated at t=0, the nature of the measurement setup causes some delay at the beginning of the measured trace prior to the first stimulus pulse). It is however possible to use the remaining signal, after about t=1.2 ms, i.e. from about 0.3 ms after completion of the stimulus, for analysis and feedback purposes in a similar way the full ECAP would be used if it were available.

FIGS. 2-6 present recordings of evoked action potentials (ECAPs) and Late Responses (LRs) measured intraoperatively in the subthalamic nucleus (STN) of patients undergoing the implantation of deep brain stimulators. In these figures the stimulus onset occurred at about 0.79 ms after t=0. FIG. 2a shows ECAPs obtained from biphasic bipolar stimulation at 130 Hz and 90 µs pulse width on electrodes 1 and 2 of a DBS electrode array (denoted 201 and 202, respectively, in FIG. 2b), and measured on electrode 3 (top plot) and electrode 4 (bottom plot of FIG. 2a) of the array (denoted 203 and 204, respectively, in FIG. 2b). The 3-peak response resembles ECAPs observed during spinal cord stimulation. The blanking period of the measurement device masks the first P1 peak on electrode 3, the electrode closest to the stimulus site. Also, peak N1 is partially truncated. The upper plot in FIG. 2a shows measured ECAPs on electrode 3, close to the stimulus site, at varying amplitudes of stimulus current. The signal is several millivolts strong for 3.5 mA stimulation and propagates away from the stimulus site. The lower plot in FIG. 2a shows measured ECAPs on electrode 4, a small distance further from the stimulus site as compared to electrode 3, at the same varying amplitudes of stimulus current. Peak P1 again is removed by truncation but N1 is more intact. While Channel 3 suffers more truncation, it receives signals of about 4 times greater amplitude than channel 4, noting the different y-axis scales in the two plots. FIG. 2a shows that the compound action potential evoked by the stimulus in the STN rises with stimulus current, and concludes within about 1.7 ms of onset of the stimulus as the action potentials propagate away from the stimulus site.

Figure 2A:
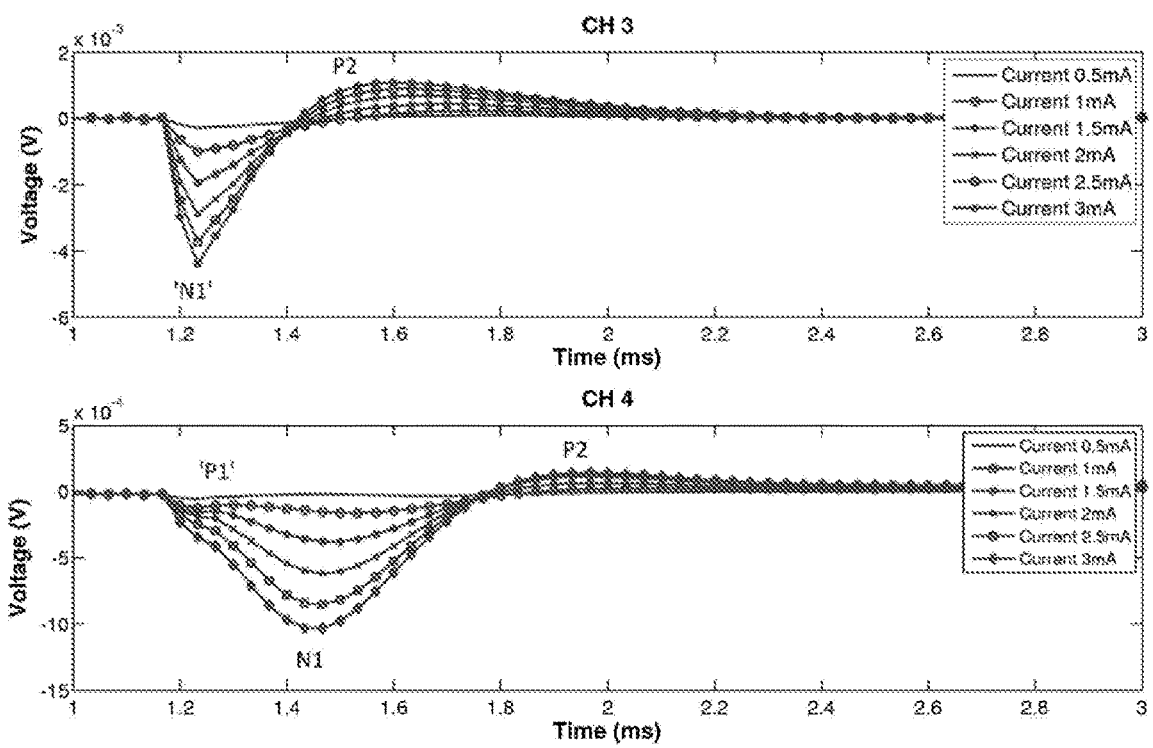
FIG. 2*a* illustrates evoked compound action potentials (ECAPs) measured on electrodes at close range to a stimulus site.
Figure 2B:
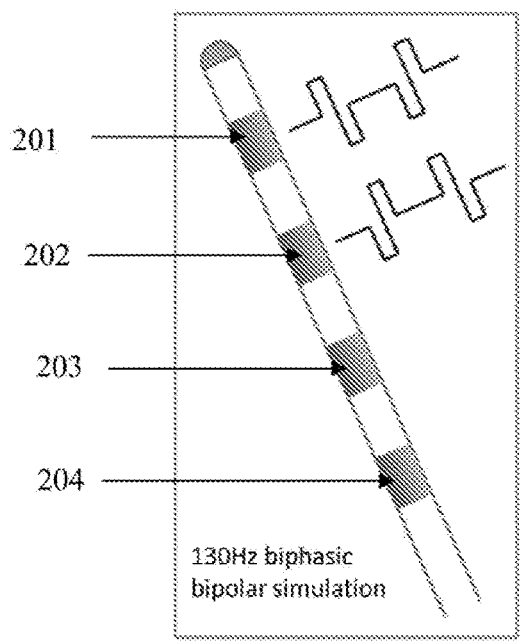
FIG. 2*b* illustrates the biphasic stimulus delivered.

FIG. 2b illustrates the biphasic stimulus delivered on electrode 1 (201) and electrode 2 (202) with an alternating polarity pattern in which the polarity of the first pulse in a biphasic stimulus changes with each impulse.

Figure 3:
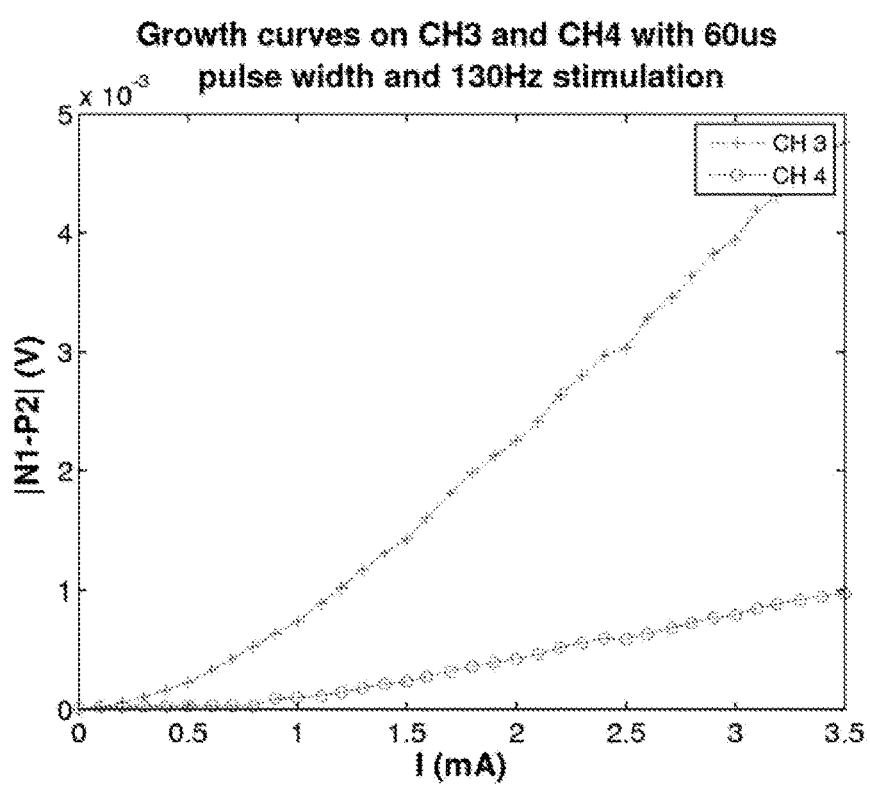
FIG. 3 shows the growth curves of the P2-N1 amplitude for a truncated and non-truncated ECAP.

FIG. 3 shows the growth curves of the P2-N1 amplitude for a truncated and non-truncated peaks in the same patient. This illustrates that the linearity is well preserved which allows for an easy calibration and feedback design to control the ECAP amplitude. Despite the truncation in channel 3, the electrode closer to the stimulus site displays larger responses when measured as |P2-N1| as compared to electrode 4, further away from the stimulus site. Thus, despite the truncation, the general characteristics of fading and smearing as the response moves away from the stimulus are preserved. For the sake of clarity, the text will use the term "ECAP" to refer to both the complete ECAP and the truncated one. In the case of the truncated ECAP, the N1-P2 amplitude is taken as shown on FIG. 2a.

FIG. 2 shows the truncated ECAPs measured on two separate channels for various stimulation intensities. It can be seen that only channel 4 displays the full N1 peak. Despite the truncation on channel 3 only, it has been shown that the |N1-P2| amplitudes both have linear growth curves with some threshold behaviour at very low stimulation intensities FIG. 3 shows growth curves of the |N1-P2| amplitude for various stimulation currents. CH3 is the electrode closest to the stimulus site, in which the N1 peak is truncated, and CH4 is the electrode furthest away from the stimulus site with an intact N1 peak. The growth curve displays a threshold behaviour below 0.5 mA stimulation and transitions smoothly to a linear regime. On E3, the slope is 1.7 mV/mA ($R^2$>0.99) and on E4 the slope is 0.37 mV/mA ($R^2$>0.99) for stimulus currents 1.5 mA and above.

In addition to the ECAP arising directly from the stimulus and concluding within about 1.7 ms of the stimulus, as shown in FIG. 2a, the present invention further recognises that a late response follows the ECAPs, and carries important information. Without wishing to be limited by theory, it is nevertheless noted that the late responses (LR), unlike ECAPs (also referred to herein as early responses), are not the direct response of the tissue but rather appear to be a systems response from the cortex and other subcortical structures projecting back into the STN. Irrespective of mechanism the present invention recognises the existence of the late response, and a range of uses and applications arising from its measurement.

The late responses are typically of much smaller amplitude than the early ECAP, and typically do not have a linear growth curve. At 130 Hz stimulation (a standard frequency for maximum efficacy), two late responses can be observed, one occurring shortly after the end of the early response, and one occurring roughly 2-3 milliseconds after the first. The present specification when describing a late response in the singular may thus encompass more than one response manifesting in the neural measurement, after the ECAP.

Figure 5:
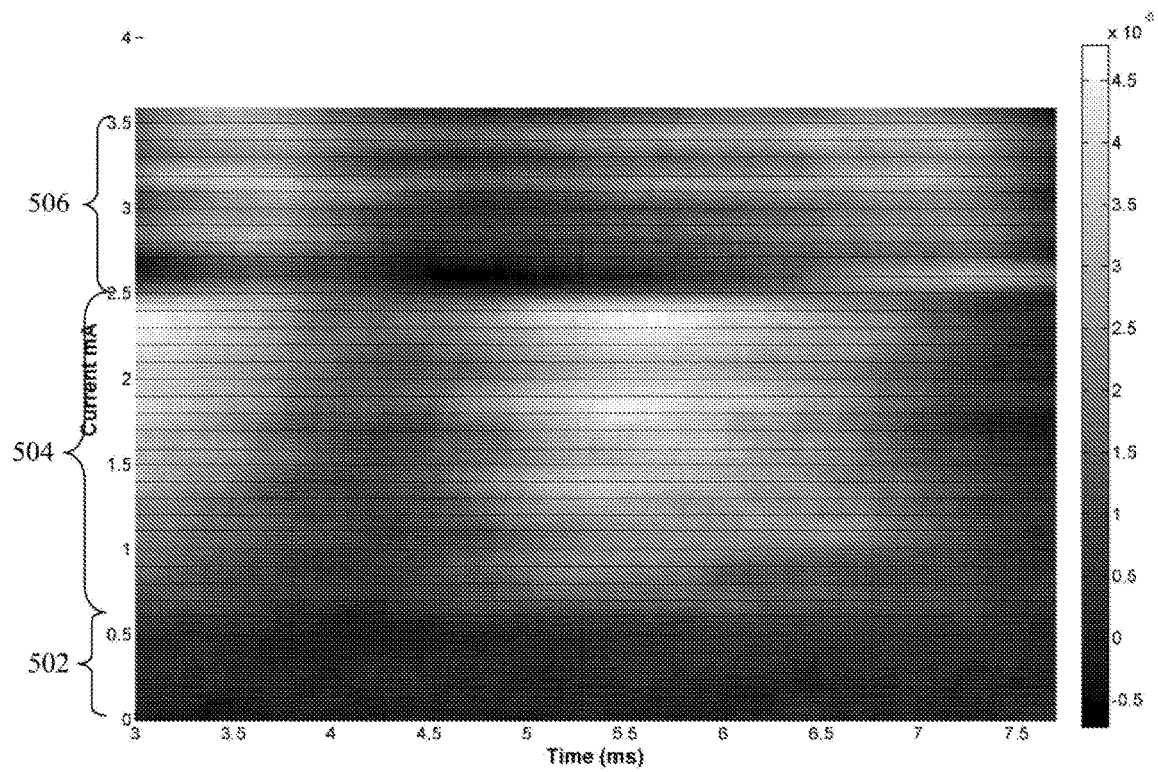
FIG. 5 illustrates the late response progressing non-linearly through three different states.

Some embodiments of the present invention further recognise that, in the case of the STN, as the stimulation current is increased the late response progresses non-linearly through three different states as shown in FIG. 5:

a. The subthreshold state 502 when the stimulation current is below about 0.6 mA, in which only a very small late response or no response at all occurs;

b. The non-therapeutic state 504 when the stimulation current is between about 0.6 mA and about 2.5 mA, in which a late response can be clearly observed between 4.5-7 ms on the time scale of FIG. 5, but in which the stimulation does not yet have therapeutic effects for the patient; and c. The therapeutic state 506 in which the stimulation current is above about 2.5 mA, which corresponds to therapeutic levels of stimulation.

Thus, the transitions from the subthreshold state to the non-therapeutic state and then to the therapeutic state are abrupt in the STN for this patient and marked boundaries can be observed in FIG. 5 when the stimulus current is increased past the two transition points. Similar non-linear states of the late response may be similarly illustrative and useful in other target structures in the brain.

Figure 4:
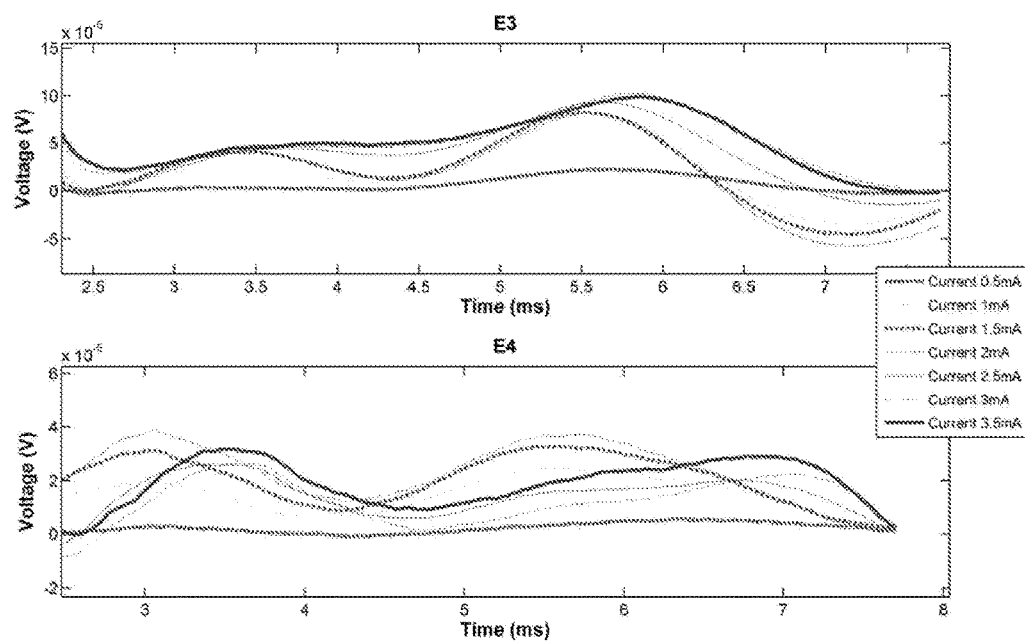
FIG. 4 illustrates the late responses for various stimulus currents.

The transition from the non-therapeutic state to the therapeutic state is characterised by a marked shift in time of around 1.5 ms of the peak of the second late response with respect to its location in time in the non-therapeutic state (see FIG. 4 and FIG. 5). FIG. 4 illustrates the late responses for various stimulus currents. The boldface traces each represent one of the states the system can be in. The late responses are an order of magnitude smaller than the ECAPs and peak roughly 1 ms and 3 ms after the end of the ECAP. For example in the lower plot of FIG. 4 the second late response peaks at about 5.5 ms when the stimulation current is 1.5 mA, but peaks substantially later at about 7 ms when the stimulation current is 3.5 mA. Thus, therapeutic stimulation is correlated with a shift in time of the late responses of around 0.5-1.5 ms. The first late response also shifts slightly (from about 3 ms to about 3.5 ms) when the transition is made, this shift is however smaller and therefore may be harder to use in a clinical setting and noisy environment. Thus, even though the shift in the first late response could be used in a similar way than the shift in the second late response, the second part of the late response presents a more distinguishable characteristic and is thus the focus of the present embodiments. Nevertheless other embodiments could additionally or alternatively address the first part of the late response.

Figure 6:
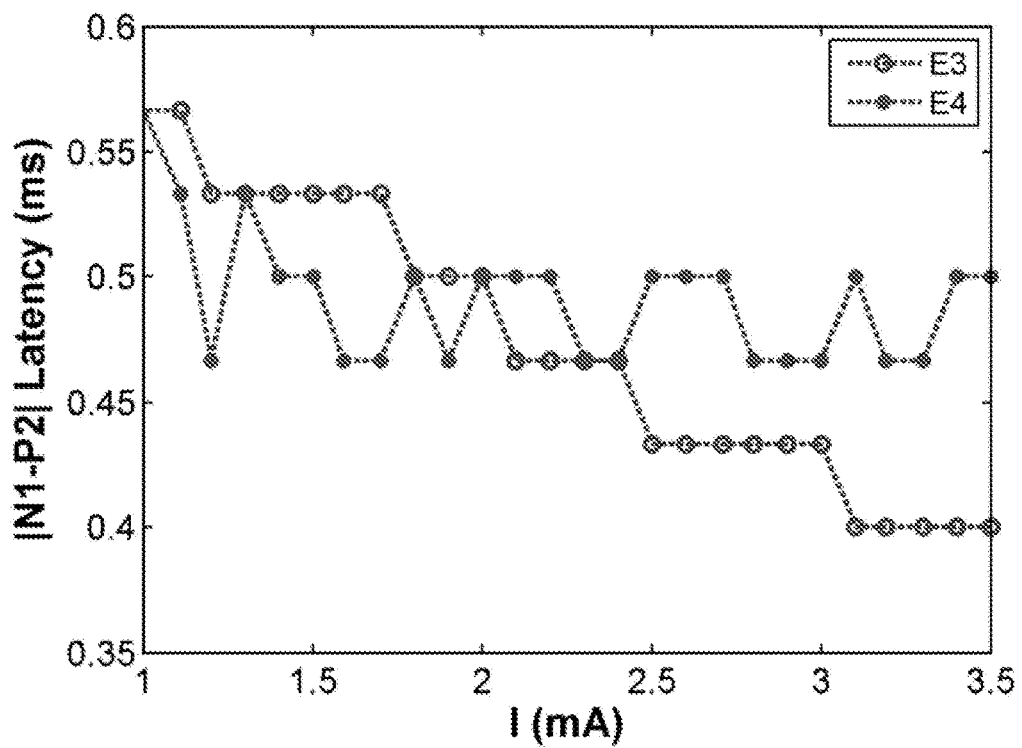
FIG. 6 illustrates the latency between the N1 peak and the P2 peak, on each of electrodes 3 and 4.

FIG. 6 illustrates the latency between the N1 peak and the P2 peak, on each of electrodes 3 and 4. This shows that the ECAPs of FIG. 2a do not spread out with increasing stimulus currents. The variations of E4 are well within the sampling error ($f_{sample}$=30 KHz). On E3 the variation is mainly due to truncation of the signal and artefact.

Figure 7:
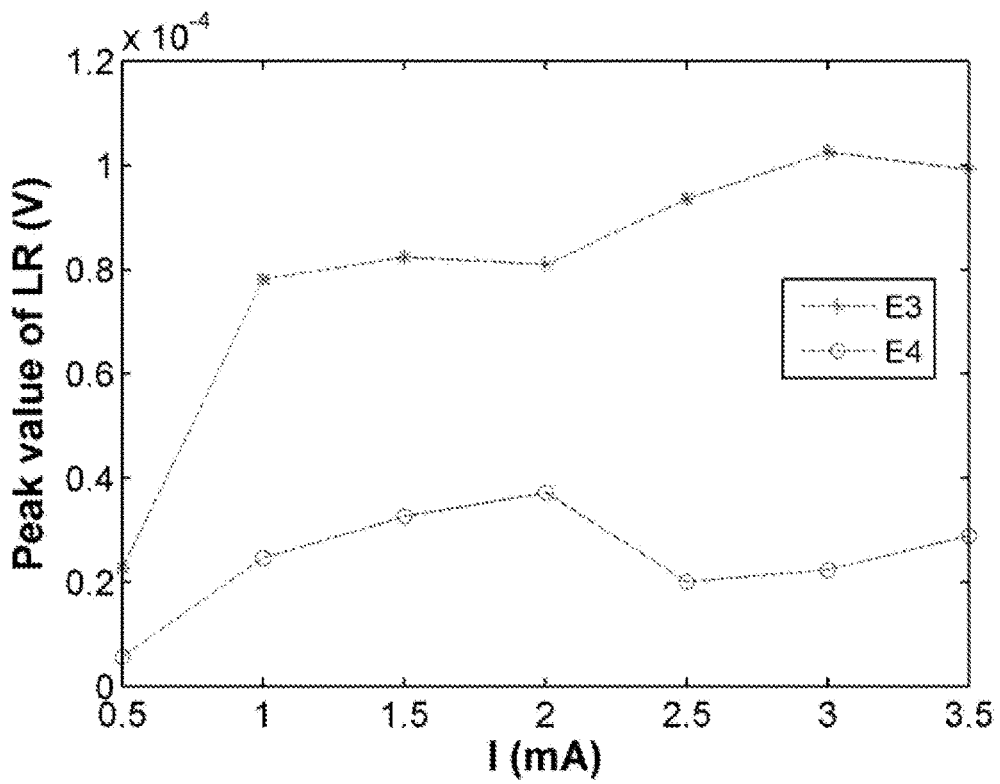
FIG. 7 shows the growth curve of the second peak of the late responses, relative to increasing stimulus current, measured on each of electrodes 3 and 4.

Unlike the early responses which as seen in FIG. 3 display a linear growth curve without plateau in the observed range (although a plateau is likely to occur at higher stimulus intensities), the late responses' amplitudes plateau very quickly. FIG. 7 shows the growth curve of the second peak of the late responses, relative to increasing stimulus current, measured on each of electrodes 3 and 4. Unlike the linearly growing ECAPs (FIG. 3), the growth curve of the late responses in FIG. 7 levels off quickly and seems to be state-dependent. The late response peak on E4 decreases in amplitude when the therapeutic state is reached and grows again within the new state. This is more conspicuous on E4 than on E3 which is closer to the stimulation site, where the size of the evoked response might mask some of the smaller responses and is likely to have decreased excitability shortly after the early response.

The neural measurements encompassing the period containing the late response(s) thus show that the responses are made up of two distinct parts: one being the ECAPs from the surrounding tissue and the second being the late responses, which may be cortical potentials projecting back into the basal ganglia. The preceding further establishes that the late responses undergo three distinct states when the stimulation current is increased: the subthreshold state where no response occurs, the non-therapeutic state in which a clear response is present but which has no therapeutic effect for the patient, and the therapeutic state which coincides with the neurologist's assessment of therapeutic levels of stimulation.

The identification of these distinct states could in turn in some embodiments be used to ease the design of feedback-enabled deep brain stimulators and provide a quantifiable way to assess the efficacy of deep brain stimulation in the surgical theatre and throughout the therapy.

The present invention thus recognises that by taking a measurement and monitoring for such a late response, a range of observations may be made. A number of such embodiments of the invention will now be discussed. In each of the systems presented below, each electrode can either be stimulating or recording. Each device will contain one or multiple leads with 2 or more electrodes on each lead. The stimulation and recording can be carried out on any given set of electrodes on each lead. Each of these systems will comprise the leads, a controllable stimulator and a processing unit that will process the recorded information and set the control parameters accordingly.

One embodiment involves parameter adjustment for DBS for Parkinson's. It is noted from FIG. 3 that the amplitude growth of the ECAP is linear over a range of currents. The slope of growth, and the threshold at which an ECAP is first detected at smallest stimulus current, both provide a measure of the excitability of the DBS structure which is being stimulated, as well as providing long term and continuous information regarding the neurological state of the target being stimulated.

This embodiment thus recognises that measurement of the ECAP amplitudes and shapes as a function of stimulation parameters provides useful information for parameter programing. Measurement of the strength duration curve by measuring the ECAP threshold at a range of pulse widths allows determination of the chronaxie and rehobase for the recruited neurons. From this, the most efficient stimulation pulse width and current can be determined. Stimulating with efficient parameters has the beneficial effect of lowering the power consumption and allowing the construction of smaller devices.

The neural response measurements can be collected and stored in the implant for later downloading. The downloading and access to the data can be achieved via a number of means, for example the clinician can download information at the time of routine follow-up. Information can be downloaded when the patient charges their system of via wireless radio (preferably MCS band) periodically. The data can be transferred to centralised databases, etc.

Figure 8:
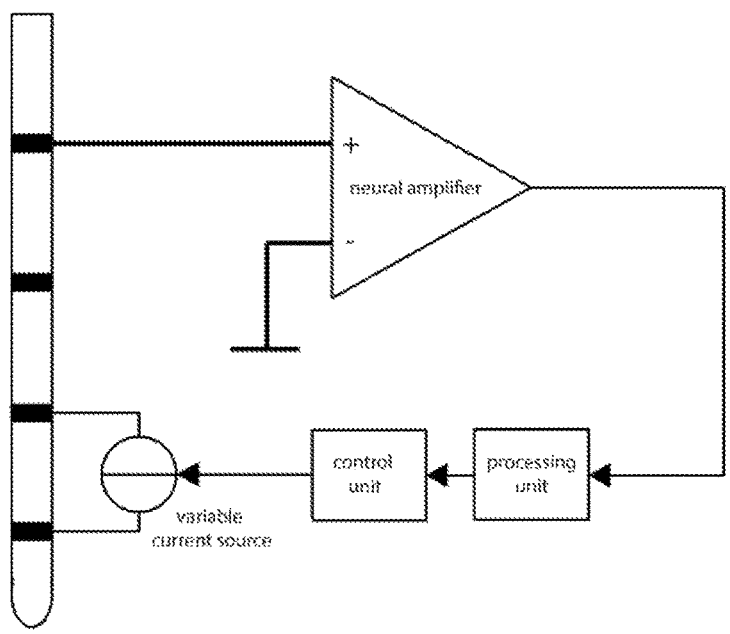
FIG. 8 is a schematic diagram of a deep brain stimulator with local feedback.

Another embodiment provides a deep brain stimulator with local feedback. The neural response measurement can be used in a closed-loop feedback system. FIG. 8 is a schematic diagram of such a feedback system using only 3 electrodes and a reference electrode for the amplifier. Once the optimal stimulation settings have been assessed, the stimulus is controlled in a way to maintain the response at a constant amplitude. This will eliminate all local effects such as heart beat and small changes in the response due to temporary or chronic metabolic changes. The responses are monitored, processed, and the stimulus adapted accordingly.

A plethora of causes can change the response of the tissue to stimulation, and may be addressed by the embodiment of FIG. 8, including:
  a. Adaptation
  b. Changes in electrode micro environment co-incident with the heartbeat
  c. A worsening of the state of the disease
  d. The course of medication intake
  e. The current overall state of the patient (sleep, rest, movement, etc.)

FIG. 8 shows an example of bipolar stimulation, in which both the stimulation and ground electrode are part of the same electrode lead. However a monopolar stimulus, in which the ground electrode is elsewhere such as on the case of the implant, is also an option in other embodiments.

In another embodiment there is provided a device to determine the efficacy of the therapy and the best stimulation settings. As noted in the preceding, the neural measurements consist of early responses (1-3 ms) and much smaller late responses (3-7 ms), and there are marked changes in the late response characteristics. For the sake of simplicity, the term "delay" when referring to the late responses denominates any measure of the relative position in time of the late responses, the ECAP or the stimulus, with respect to each other.

In the past, during the implant of a DBS system a neurologist will assess the efficacy of the treatment by gauging the felt resistance of the patient's arm to movement alongside other motor tests such as pronate/supinate hand movements, and side effects are also monitored. This previous technique is subject to human error and has a large error margin. The observation of the late responses in the present embodiment of the invention instead allows the efficacy of the treatment to be assessed during the surgical procedure. This has several benefits, including eliminating human judgement (and human error) by presenting a measurable quantity, namely the delay between the late responses or a change in the late response.

Moreover, lesions caused by surgical electrode insertion can partly or entirely suppress patient symptoms, temporarily. As a consequence, at the time of insertion when such temporary effects occur it can be difficult to assess the efficacy of the electrode placement, because only imaging and observed side effects can give an indication of the lead placement. Observing the late responses in accordance with the present invention may thus in some embodiments be used to assist with lead placement.

The late response measure in many embodiments carries the further advantage that it presents a quantifiable measure which is available in real-time to assess the overall efficacy of the treatment, eliminating or reducing the need for a long trial period with repeated device adjustments by a clinician over many weeks or months to optimise device operation, a process which is costly and subjective. Another benefit is to determine the optimal stimulation current which minimises power consumption, thus increasing the battery life of the device and decreasing the risk of damaging the tissue due to prolonged exposure to chronic stimulation.

It is to be appreciated that other embodiments may be applied to any disorder displaying similar features in the late responses. DBS is used for a whole range of diseases including Huntington's disease, Tourette's syndrome, chronic depression, dependence, tremor, Alzheimer's disease and dystonia, all of which are thought to be caused by disruption of the normal neural pathways leading to a "disease state" which could then be acted upon by deep brain stimulation.

Yet another embodiment applies late response (LR) feedback. The recording of the late responses is used in a feedback system capable of monitoring the responses and adapting the stimulation intensity for changes in the response. Changes in posture, movement, time and the development of the disease, and all sorts of other physiological and environmental factors change the response of the nervous tissue to the same stimulus. The feedback device in this embodiment therefore records the delay or other changes of the late responses and adapts the stimulation intensity to achieve maximum therapeutic effect with minimum stimulation current. The targeted stimulation current is the smallest current in which the late responses are in the therapeutic state.

The circuit diagram shown in FIG. 8 applies to this embodiment as well, albeit with distinctions in the way the processing unit drives the controller.

Figure 9A:
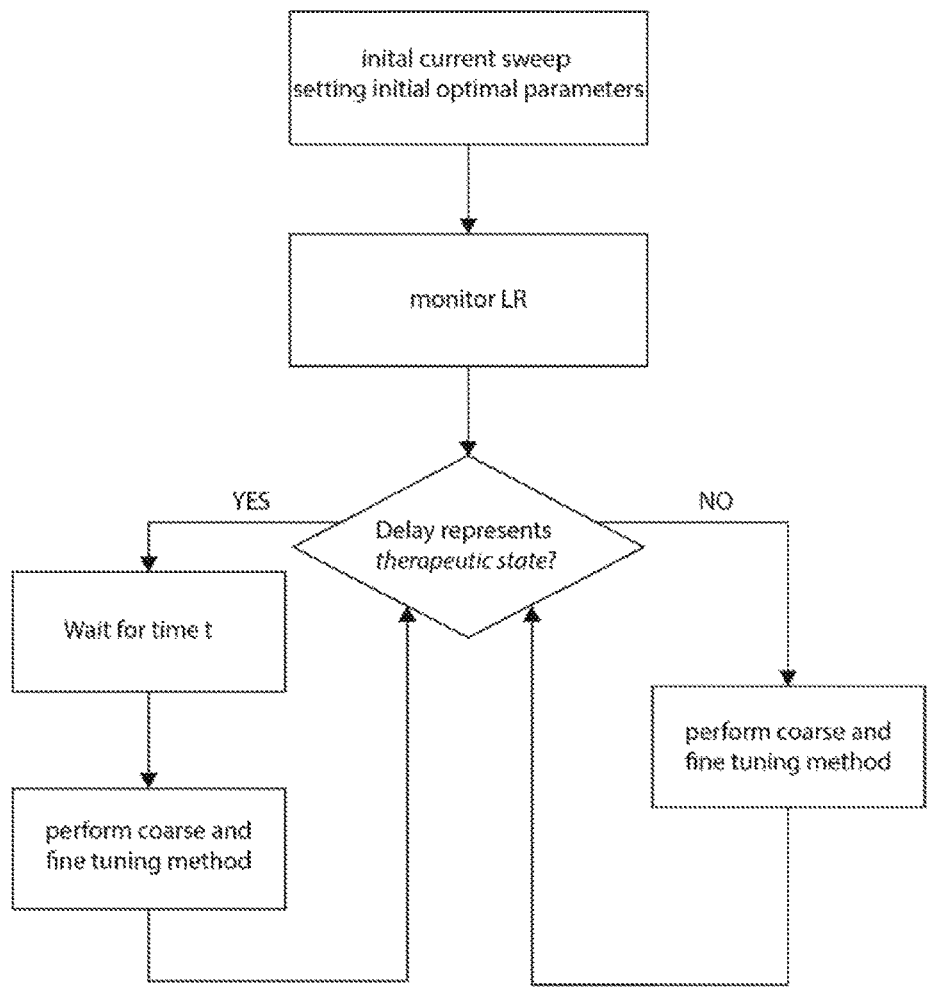
FIG. 9 is a schematic diagram of a deep brain stimulator with local feedback via simple tuning mechanism.
Figure 9B:
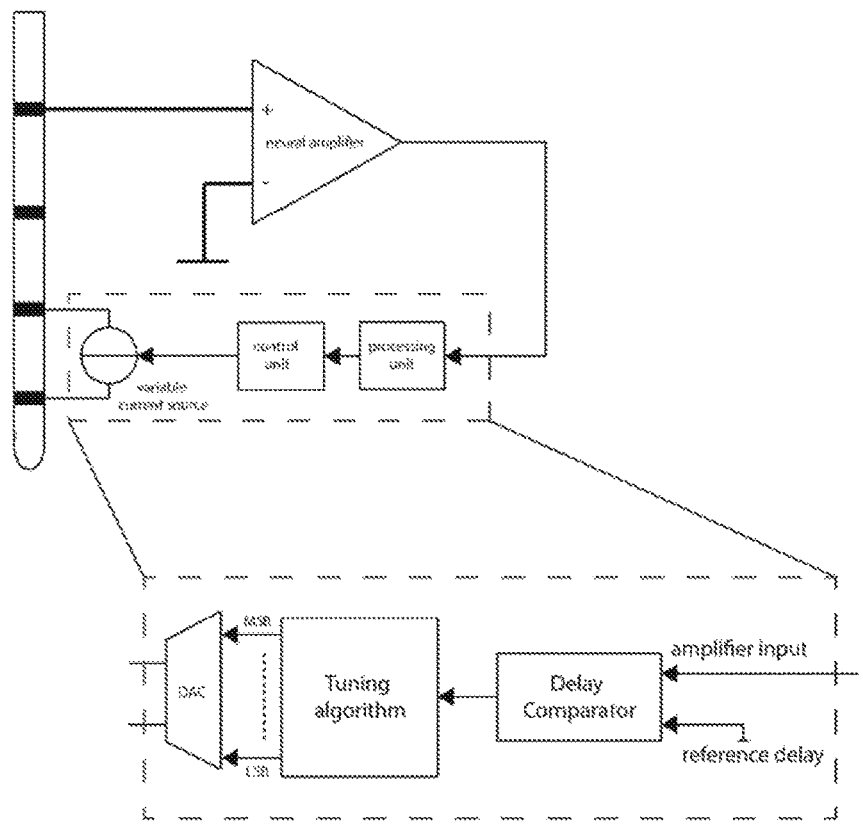

In FIGS. 9a and 9b the stimulator with local feedback uses the amplitude information of the late response and locks it to a determined value. A feedback system using the late responses will measure the latency of the late responses and adapt the stimulus intensity accordingly. One possible implementation would be the use of a simple tuning mechanism. Those mechanisms are widely used in all kinds of electronics applications, notably in variable DC sources. In its simplest form, an arbitrarily long word defines the current between two pre-set limits. The bits are then recursively modified to approach the optimal stimulation level by observing the late responses. If the latency fits the therapeutic state the next bit will decrease the current, if the late response latency indicates that stimulation is in the sub-therapeutic state then the current is increased. Thus the system uses a simple comparator and digital controller.

In other embodiments, the embodiment of FIG. 9 may be altered so as to monitor the late responses only occasionally, instead of monitoring the late responses at all times. This allows a trade-off between stimulation power consumption and processor power consumption to be optimised. In such embodiments, a periodic or occasional sweep of stimulus current around the existing stimulation level may be performed, to minimise stimulus current while remaining in a therapeutic state. Also, stimulus current will be immediately adjusted if the late responses shift into a non-therapeutic state.

Yet another embodiment is illustrated in FIG. 10, comprising a hybrid feedback system. As the late responses are very small compared to the early responses and are therefore subject to noise and large variations, a hybrid feedback system is proposed which automatically sets the stimulation intensity to optimal levels by:
  a. Recording and processing (averaging, will need some memory) the late responses and finding the optimal stimulation intensity.
  b. Recording the amplitude of the ECAP at that stimulation level
  c. Applying closed-loop feedback on the ECAP The device of FIG. 10 will perform periodic or occasional current sweeps as discussed above.

Figure 10A:
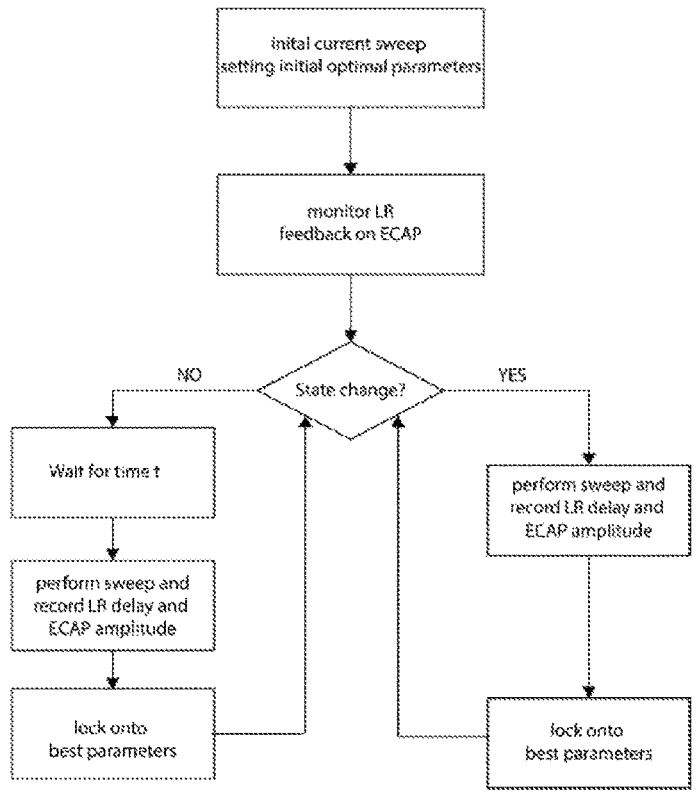
FIG. 10 illustrates a hybrid feedback system.
Figure 10B:
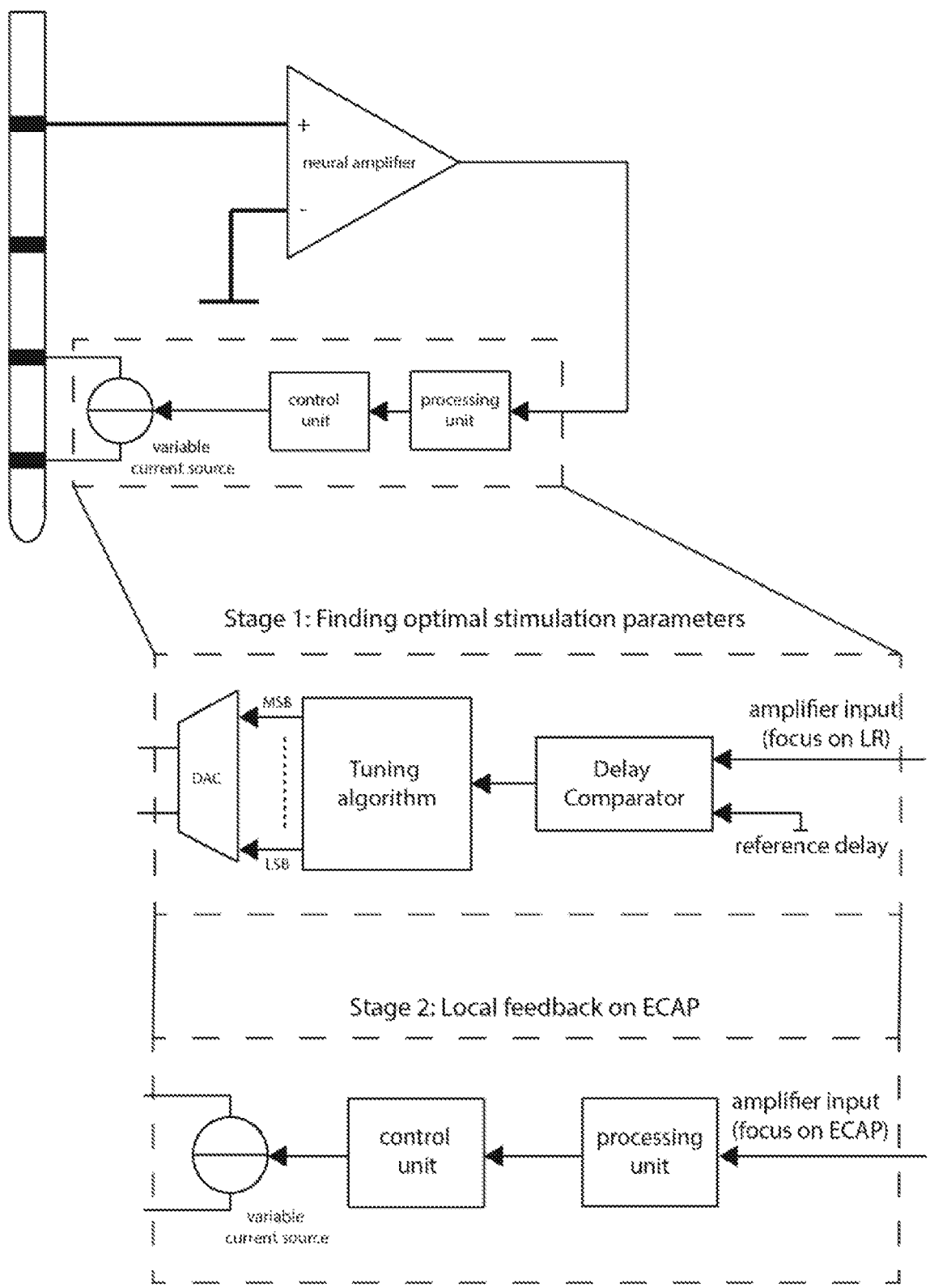

The device of FIGS. 10a and 10b utilises a 2-stage control-system in which stage 1 finds the best stimulation setting, similarly to the Late Response Feedback presented above. Once the setting is found, local feedback is applied using the ECAP amplitude. As the late responses are of much smaller amplitude and more subject to noise, an accurate characterisation of the delay requires memory and computing power which will decrease the battery life of the implant. This hybrid feedback system will consume less power as the computationally heavy tasks can be made arbitrarily sparse.

Figure 11A:
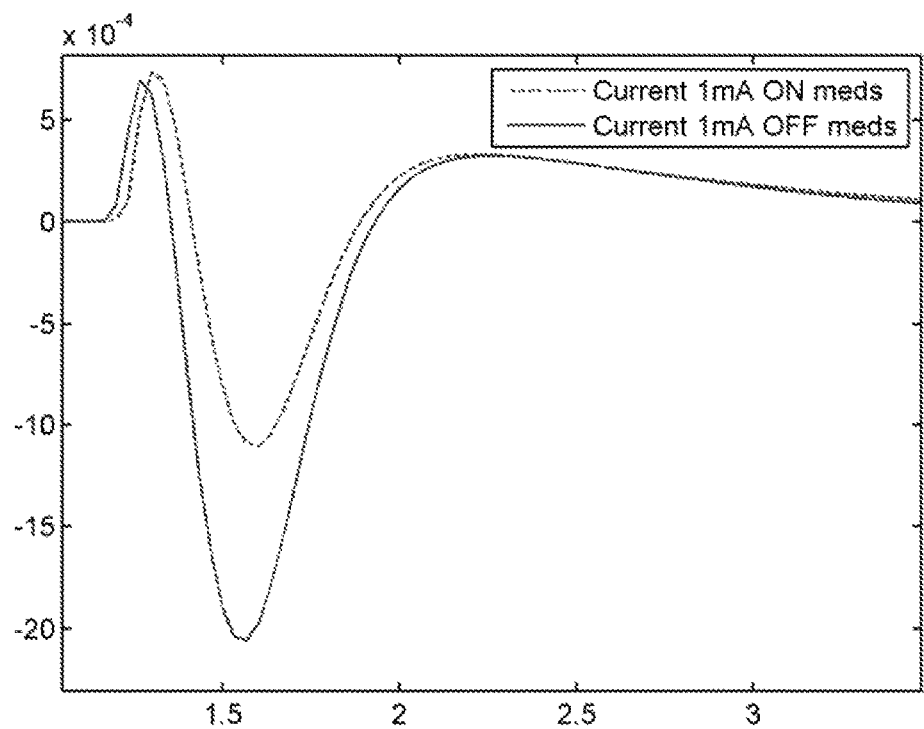
FIGS. 11*a* and 11*b* illustrate that under medication the amplitude of the ECAPs is markedly decreased.
Figure 11B:
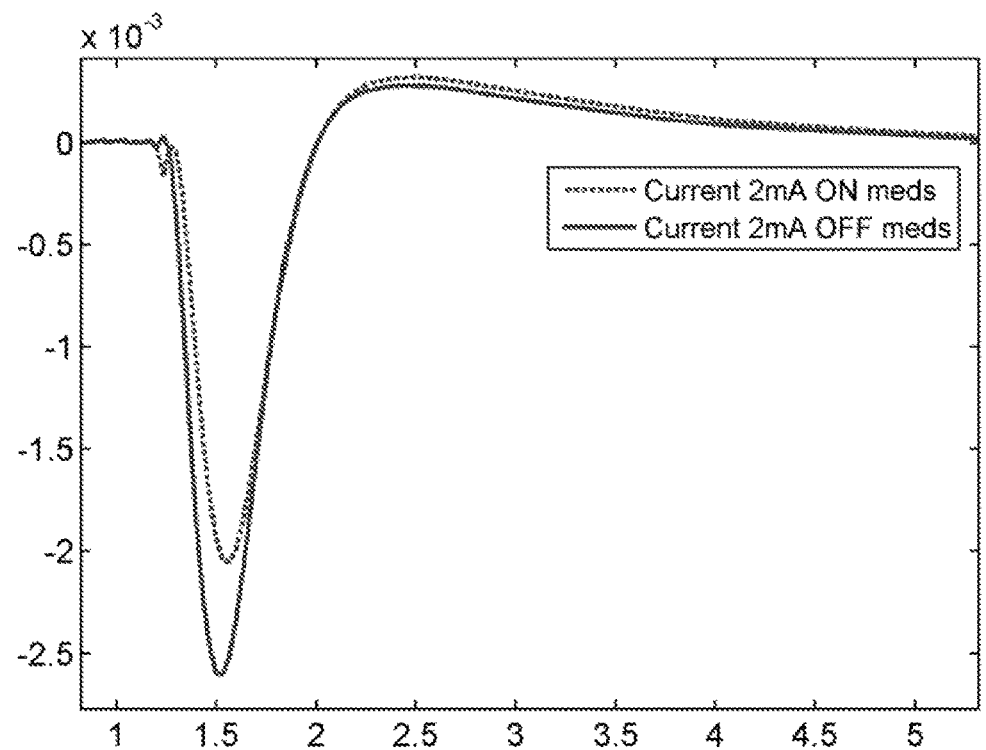
Figure 12A:
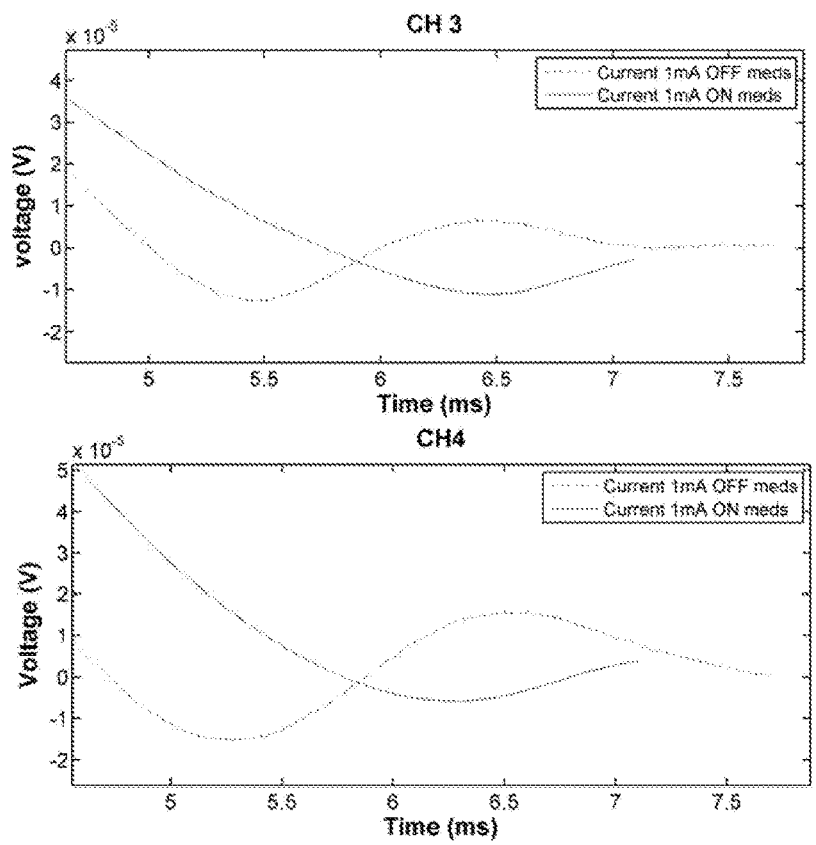
FIG. 12 illustrates late responses for various stimulation currents in a patient on and off medication.
Figure 12B:
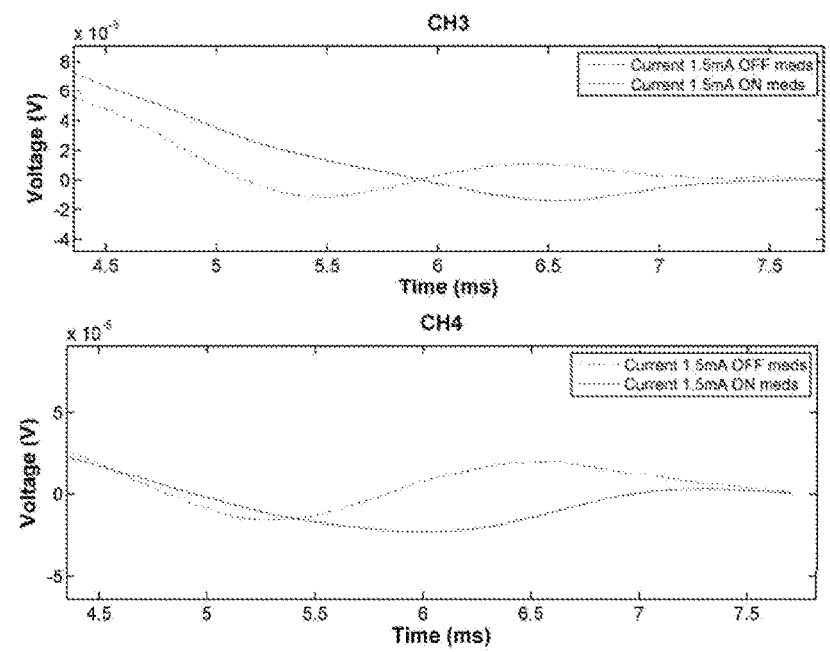
Figure 12C:
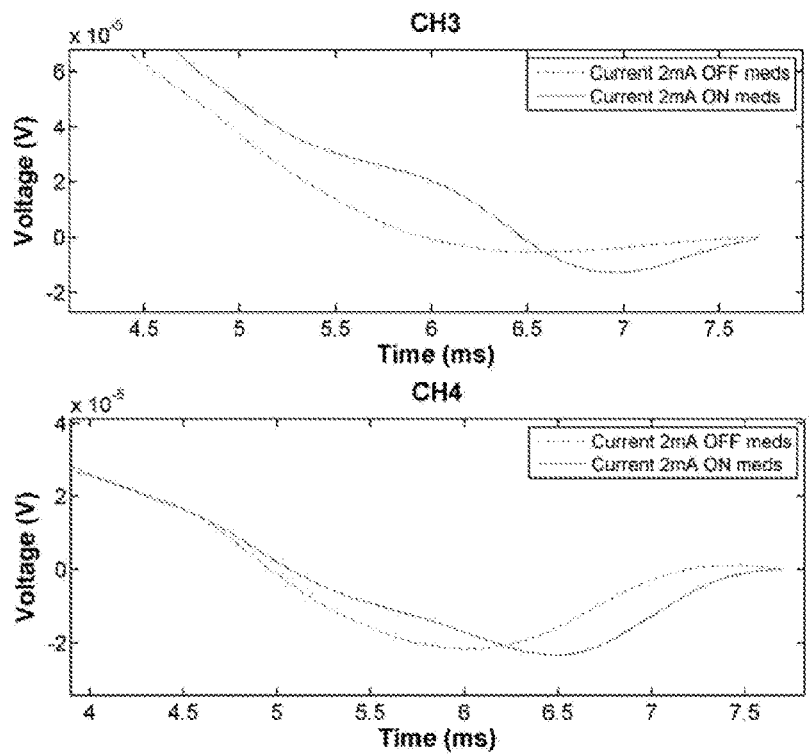
Figure 12D:
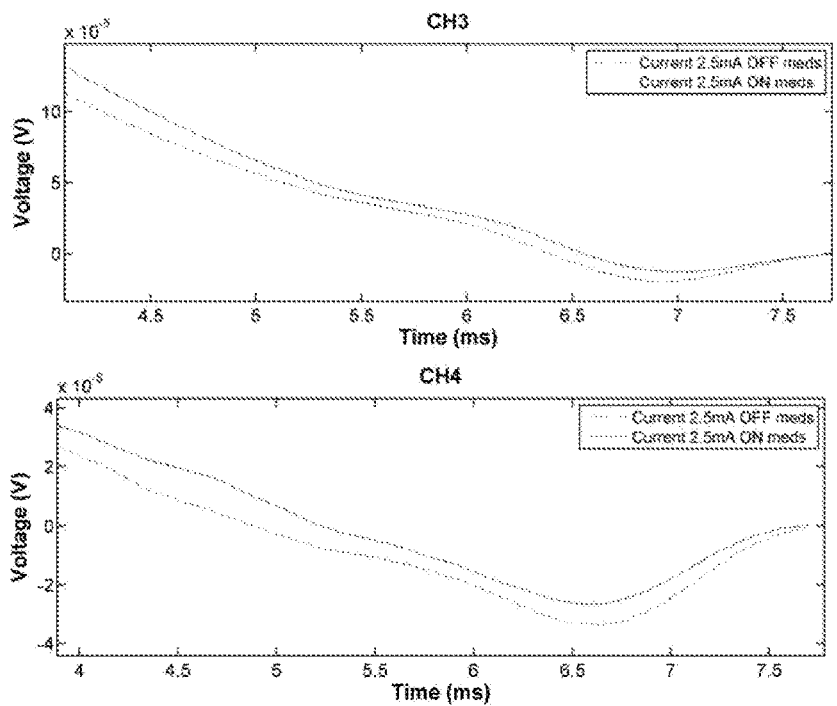

In yet another embodiment, the concentration and efficacy of dopamine is detected. Dopamine concentration has an impact on the shape of action potentials. As shown in FIGS. 11a and 11b, in a patient under medication the amplitude of the ECAPs is markedly decreased, especially for lower stimulation currents. The device can be used to characterise the dopamine concentration in the STN by measuring the shape of the ECAP and the late responses (amplitude, distances between P1, N1 and P2, distances between ECAPs and LRs). In the case of patients with Parkinson's disease, this information can be used to assess the state of the disorder and adjust the levels of levodopa administration.

The vast majority of DBS patients for Parkinson's disease require the continuing administration of Levodopa to manage their symptoms. The adjustment of the level of Levodopa in combination with DBS can be a protracted affair and can take several visits to the clinician and a number of adjustments before a stable condition is found. Knowledge of the variation in the ECAP and the late responses with Levodopa administration could be used to determine optimal dosage levels for the patient.

The measurements of FIG. 11 show that in a patient currently under medication, the amplitude of the ECAPs is markedly decreased, especially for lower stimulation currents. The growth curve can therefore be used to assess the effect of Levodopa administration. This information can be used to adapt the dosage of Levodopa as well as monitor the course of the disease.

The late responses do not show any changes in amplitude with medication or without. The latency of the late responses however shifts markedly, from one case to the other. This information can be used alone or in conjunction with the ECAP data to assess the course of the disease and the effects of Levodopa administration. FIG. 12 illustrates late responses for various stimulation currents in a patient on and off medication. The late responses shift to the same position once the treatment becomes therapeutically effective and therefore does not compromise the above feedback systems presented.

Figure 13:
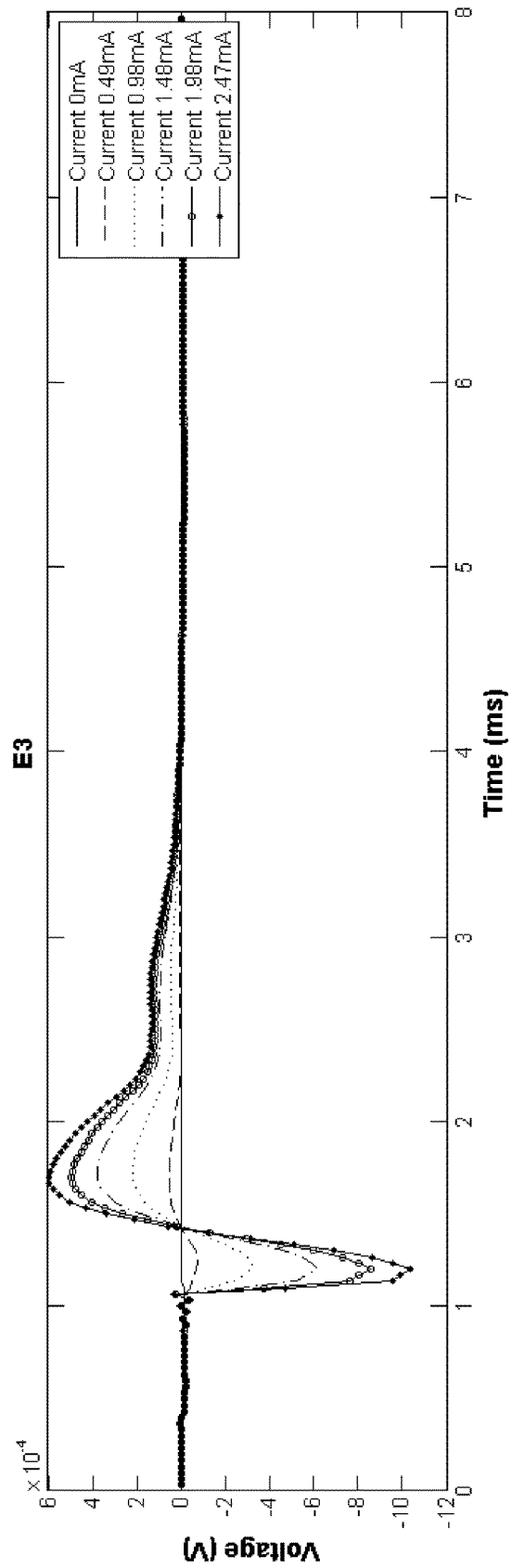
FIG. 13 illustrates neural response measurements obtained from a patient being treated with deep brain stimulation of the ventral-intermediate nucleus of the thalamus.
Figure 13:
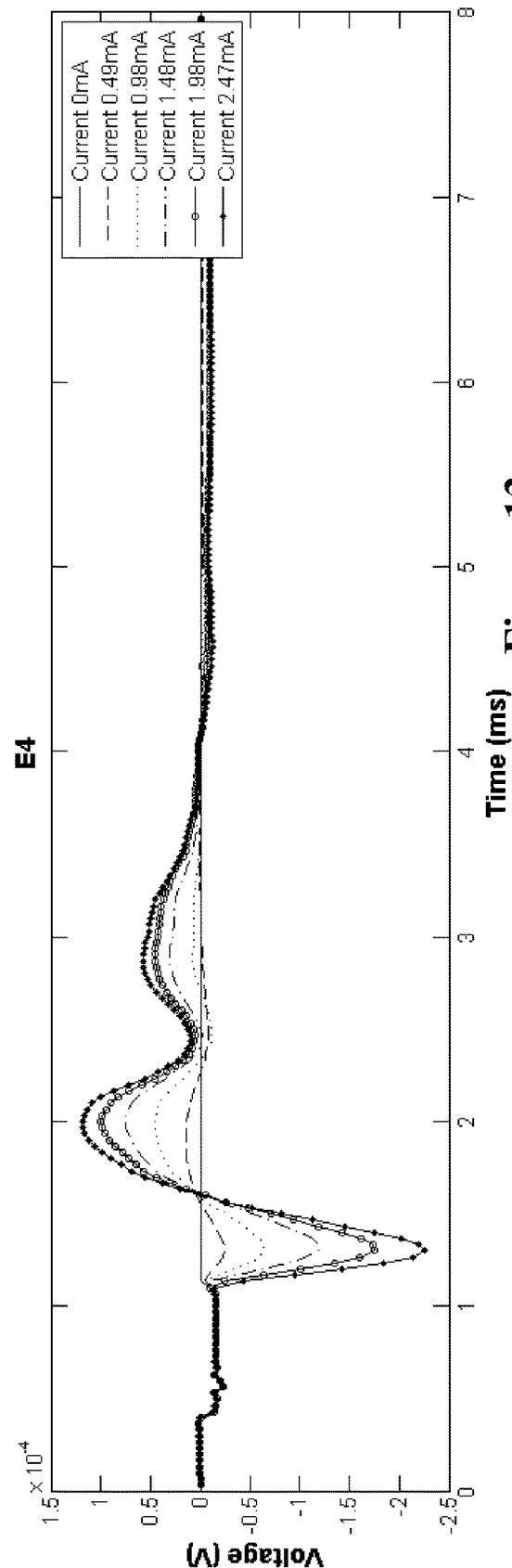

Further data was obtained of the late response in DBS recipients. FIG. 13 illustrates data obtained from a patient with Klinefelter syndrome being treated for Essential Tremor with vim (ventral-intermediate nucleus of the thalamus) DBS. Prior to the surgery and during the entire length of the experiments, the patient was OFF medication. Electrodes 1-4 are on the left side and electrodes 5-8 on the right side. FIG. 13 illustrates the neural responses measured in response to varying stimuli. No late response is observed in response to such a stimulus regime of the thalamus, indicating that the results obtained in respect of the STN as discussed in the preceding are not mere artefact but are a specific characteristic of that structure, confirming that the late response, when present in a brain structure, presents a functionally relevant marker to monitor.

Figure 14A:
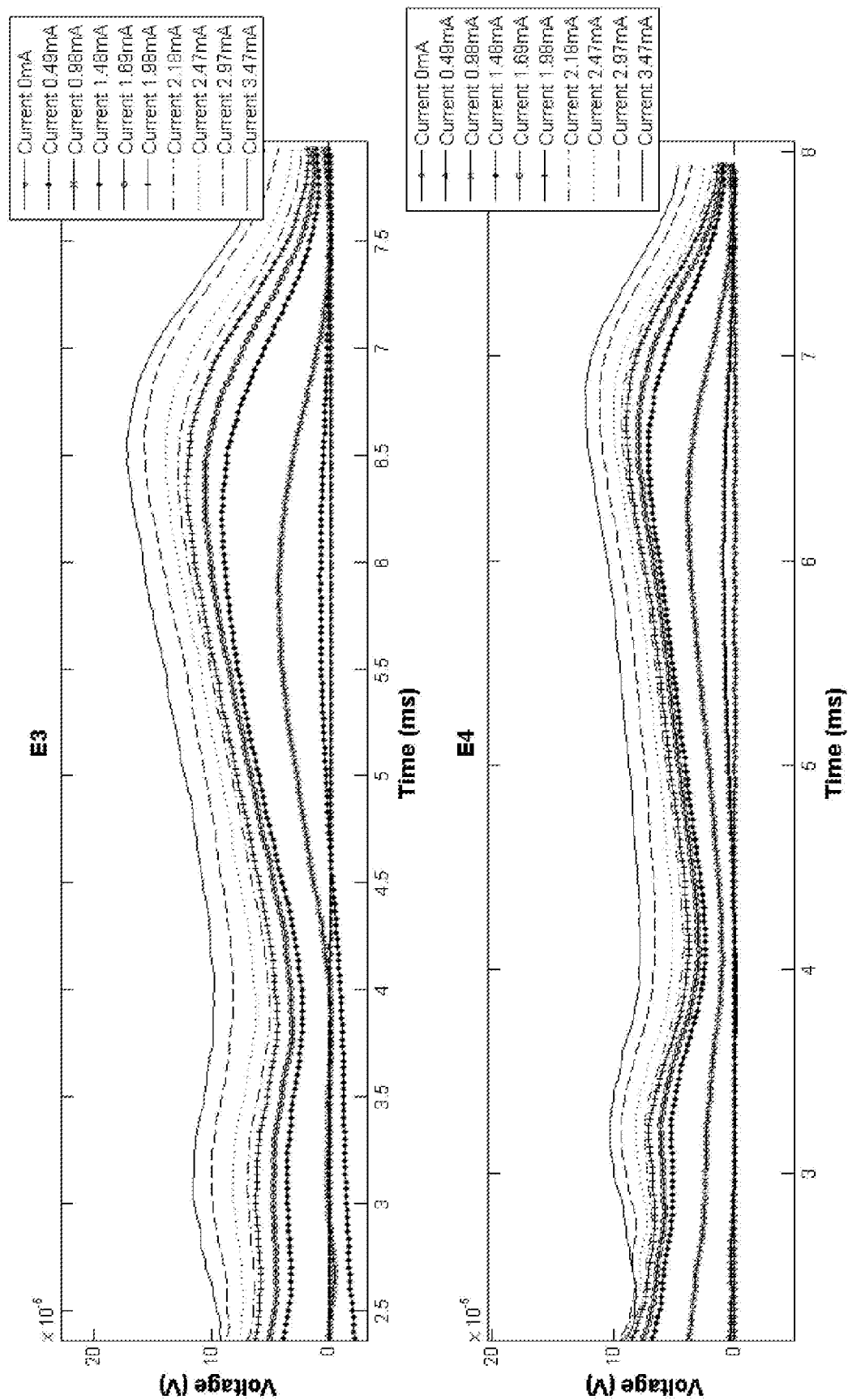
FIG. 14 illustrates data obtained from electrodes 3 and 4 in the left hemisphere of a patient treated with STN DBS, with FIG. 14*a* showing the neural response measurements from each electrode, FIG. 14*b* being a plot of late response latency against stimulus current, and FIG. 14*c* being a plot of late response amplitude against stimulus current.
Figure 14B:
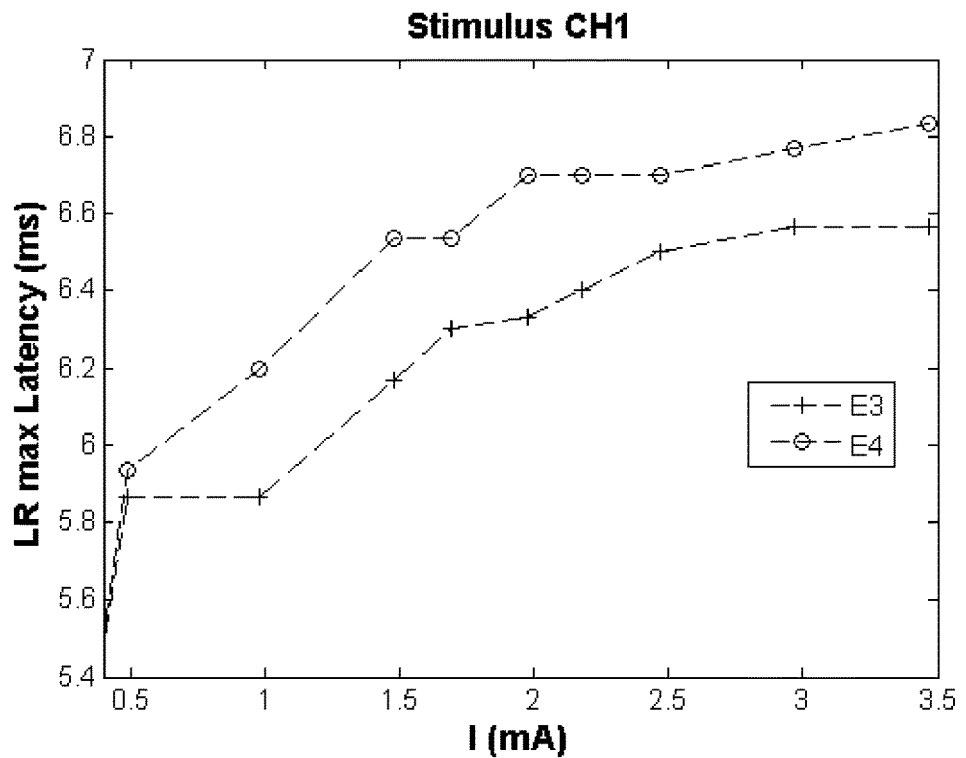
Figure 14C:
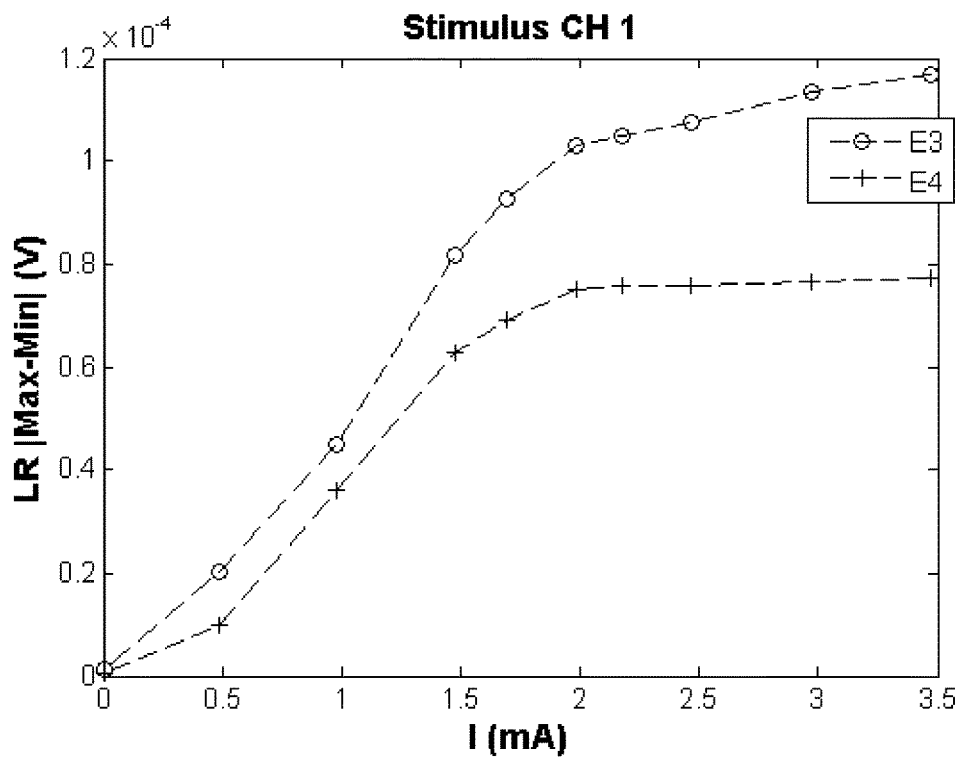

FIGS. 14-16 illustrate data obtained from a Parkinson's disease patient treated with STN DBS, similarly to the patient reflected in FIGS. 3-7. FIG. 14 relates to data obtained from E3 and E4, situated in healthy tissue in the left hemisphere. The late responses shown in FIG. 14a exhibit an increased latency with increasing stimulus current (FIG. 14b) and a non-linear amplitude growth with increasing stimulus current (FIG. 14c).

Figure 15A:
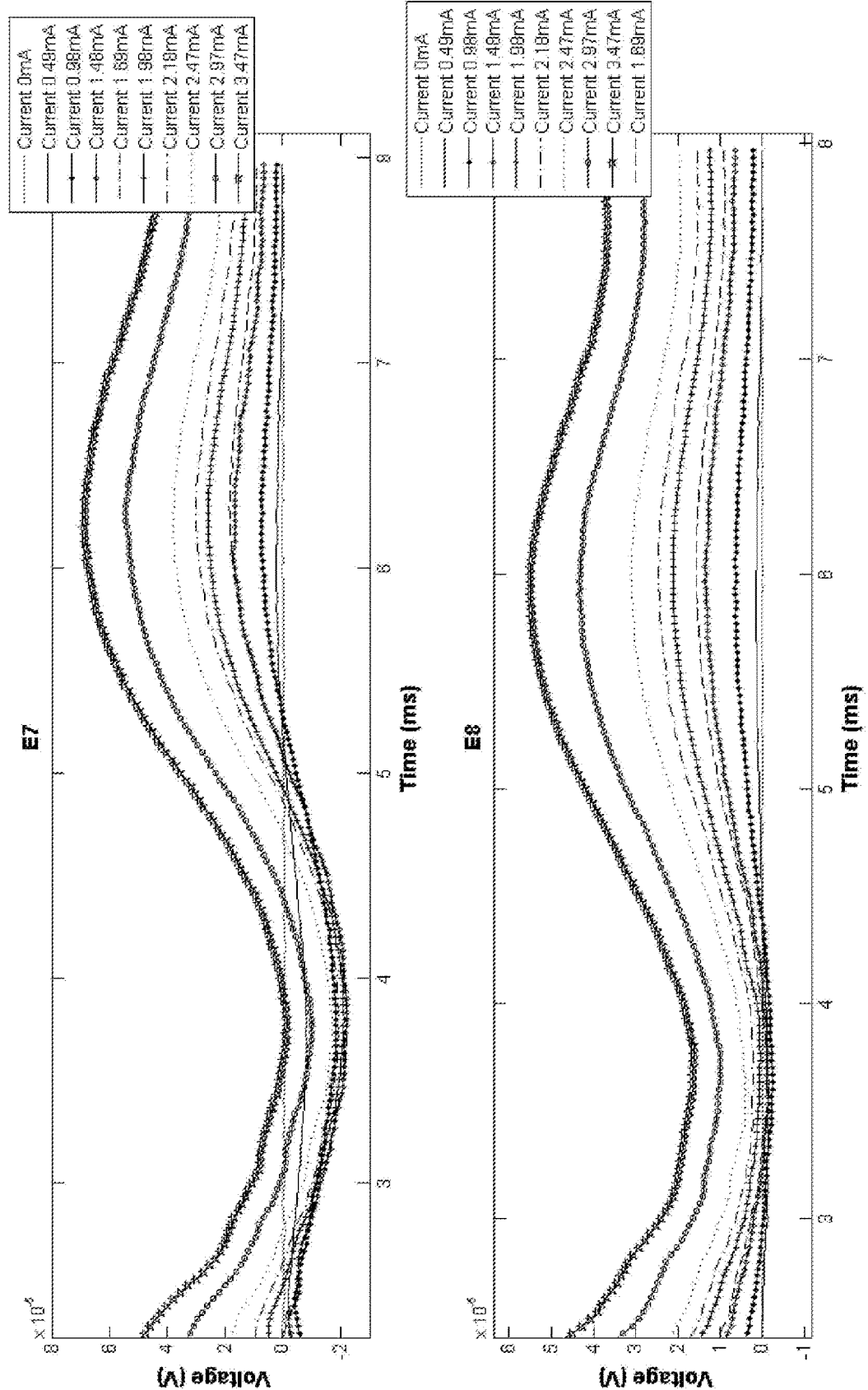
FIG. 15 illustrates data obtained from the same patient as FIG. 14, from electrodes 7 and 8 in the right hemisphere which was atrophied, with FIG. 15*a* showing the neural response measurements from each electrode, FIG. 15*b* being a plot of late response latency against stimulus current, and FIG. 15*c* being a plot of late response amplitude against stimulus current.
Figure 15B:
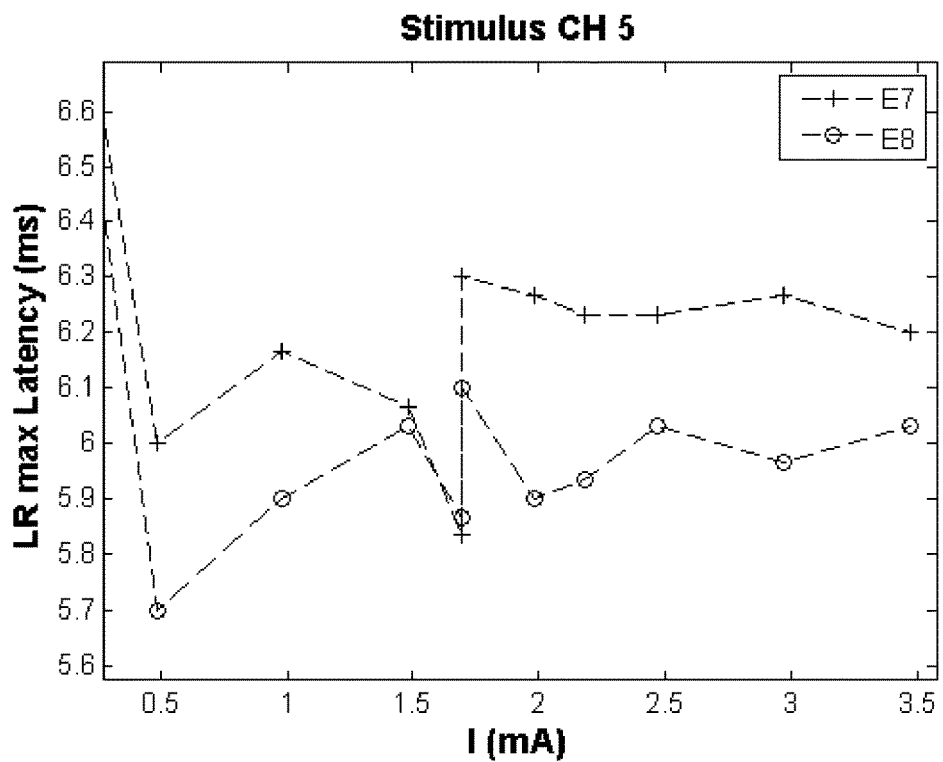
Figure 16B:
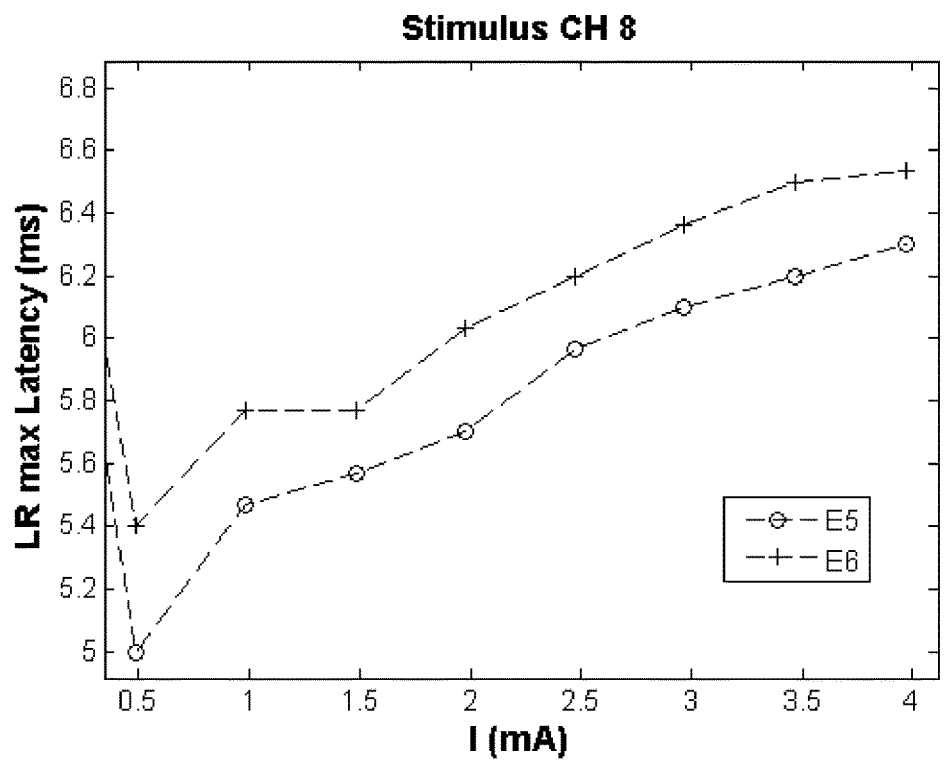
FIG. 16 illustrates data obtained from the same patient as FIGS. 14 and 15, from electrodes 5 and 6 in the right hemisphere, with FIG. 16*a* showing the neural response measurements from each electrode, and FIG. 16*b* being a plot of late response latency against stimulus current.
Figure 16A:
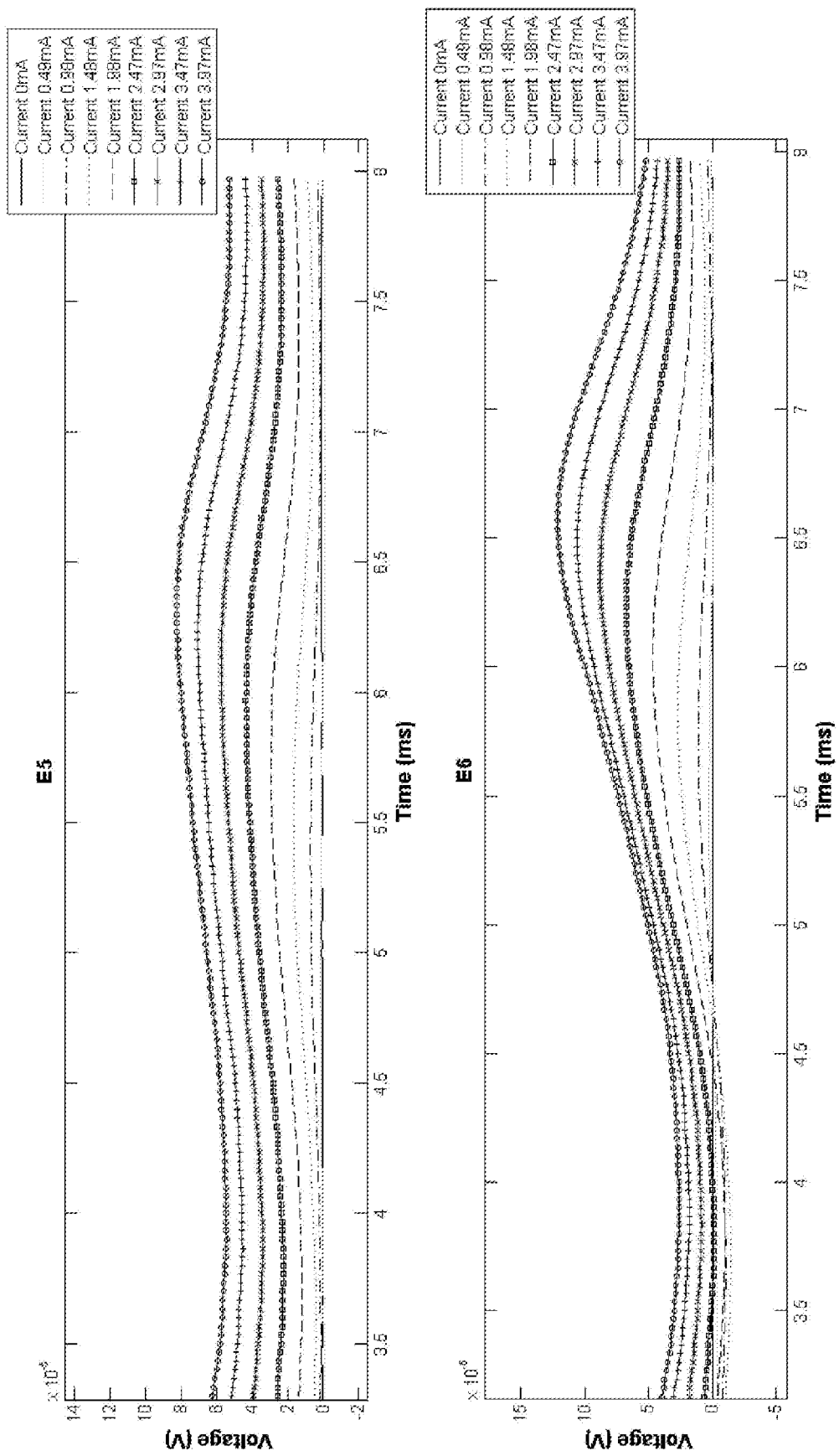

However, in contrast, the patient the subject of FIGS. 14-16 had "holes" or atrophies visible in imaging of the right hemisphere STN, near the most postero-ventral electrode, i.e. the deepest electrode, denoted E5 herein. As shown in FIG. 15, stimulating next to those holes had no effect, which was reflected in the absence of a shift of the late responses measured by E7 and E8, shown in FIG. 15. In particular, the late responses shown in FIG. 15a do not exhibit an increased latency with increasing stimulus current (FIG. 15b) which again is indicative that the change in latency of the late response reflects a neural systems response from the cortex and other subcortical structures and not merely local electrostatic effects or the like, and can thus be considered as a "control". This is further illustrated when stimulating on E8 and measuring on E5 and E6 as shown in FIG. 16. The shift in latency of the late responses recorded in FIG. 16a is more gradual than that seen in the left hemisphere in FIG. 14, which may suggest that the observed atrophies hinder the normal late response mechanism. FIG. 16b indicates the relationship of later response latency to stimulus current when stimulating on E8 which, compared to FIG. 14b, shows a slower growth. Moreover, the late response on E6 (which is closer to the stimulus site) occurs later than the late response on E5 (which is further away from the stimulus site) which is the reverse of the situation in FIG. 14.

Figure 17A:
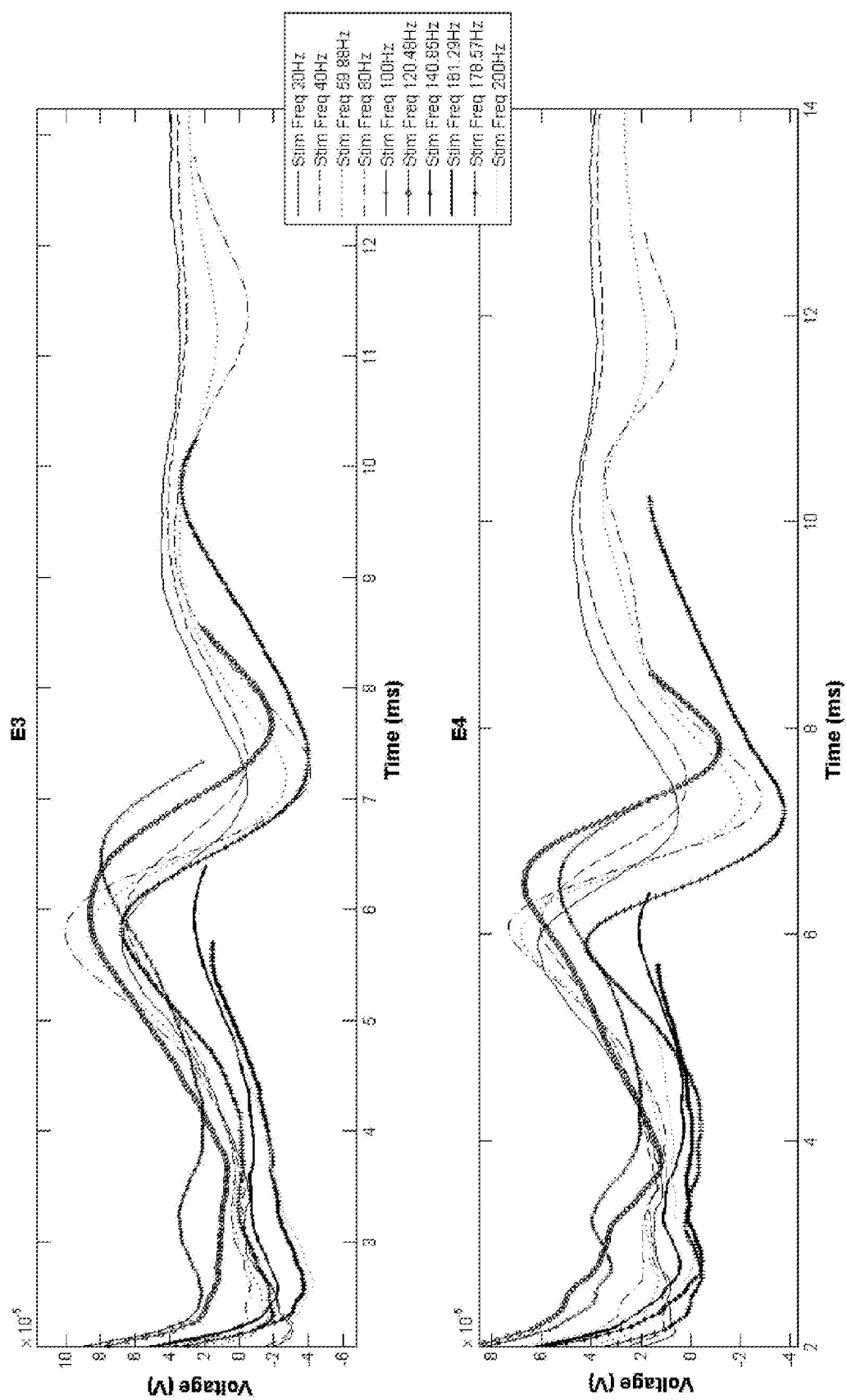
FIG. 17*a* illustrates late responses recorded in healthy tissue in the same patient as FIG. 14-16, for a constant stimulus amplitude but varying frequency.
Figure 17B:
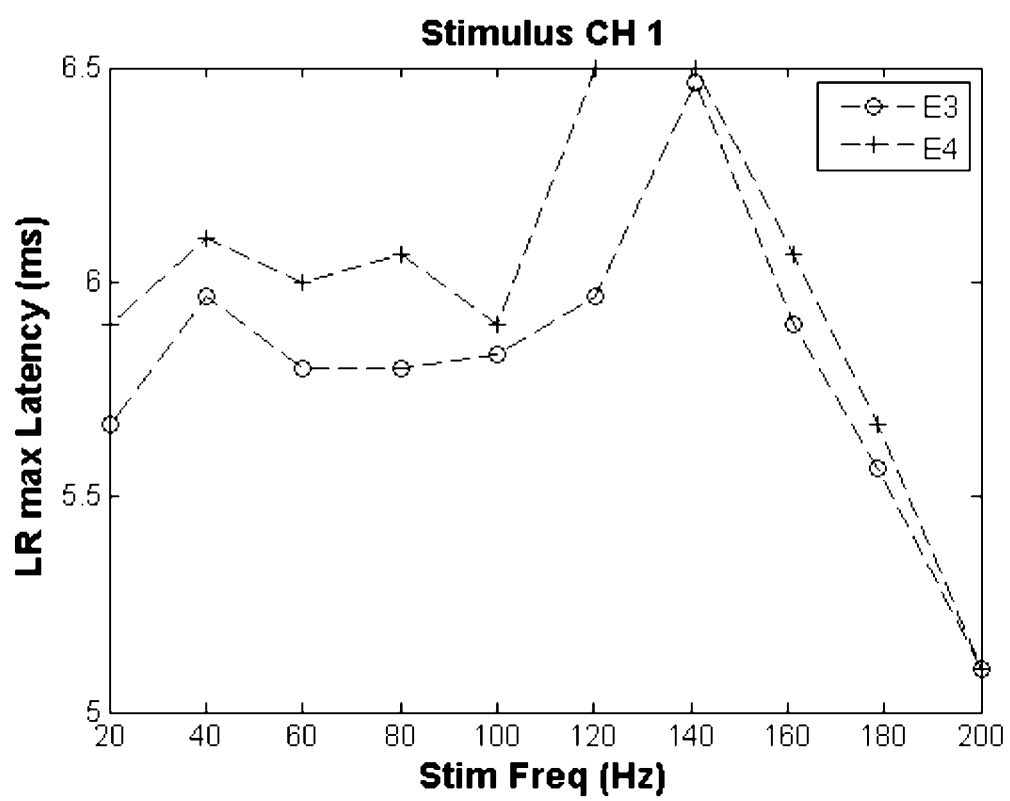
FIG. 17*b* is a plot of the latency of one of the late response peaks against stimulus frequency.

FIG. 17a illustrates late responses recorded in healthy tissue in the same patient as FIG. 14-16, for a constant stimulus amplitude but varying frequency. FIG. 17b illustrates the progression of latency of the late response peak arising at around 5.5 ms, with increasing stimulus frequency. As seen in FIG. 17b, a shift in latency of this particular peak occurs at around 130 Hz. It is noted that above about 160 Hz the length of the measurement phase is too short and the next pulse occurs before the late response can occur.

FIG. 17a also illustrates that there are more late responses than the two responses observed at 130 Hz such as in FIG. 4. FIG. 17a reveals late responses not only at around 5.5-6 ms but also at around 8 ms, 10 ms and 13 ms although the amplitude of the latter 3 responses is about 5 times smaller, or less, so the more useful marker appears to be the late response observed around 6 ms.

Comparison of the progression of the late response in different patients thus reveals that it is a change in the late response with changing stimulus that is useful to look for, which could be either an earlier response, or a later response, for example.

Figure 18:
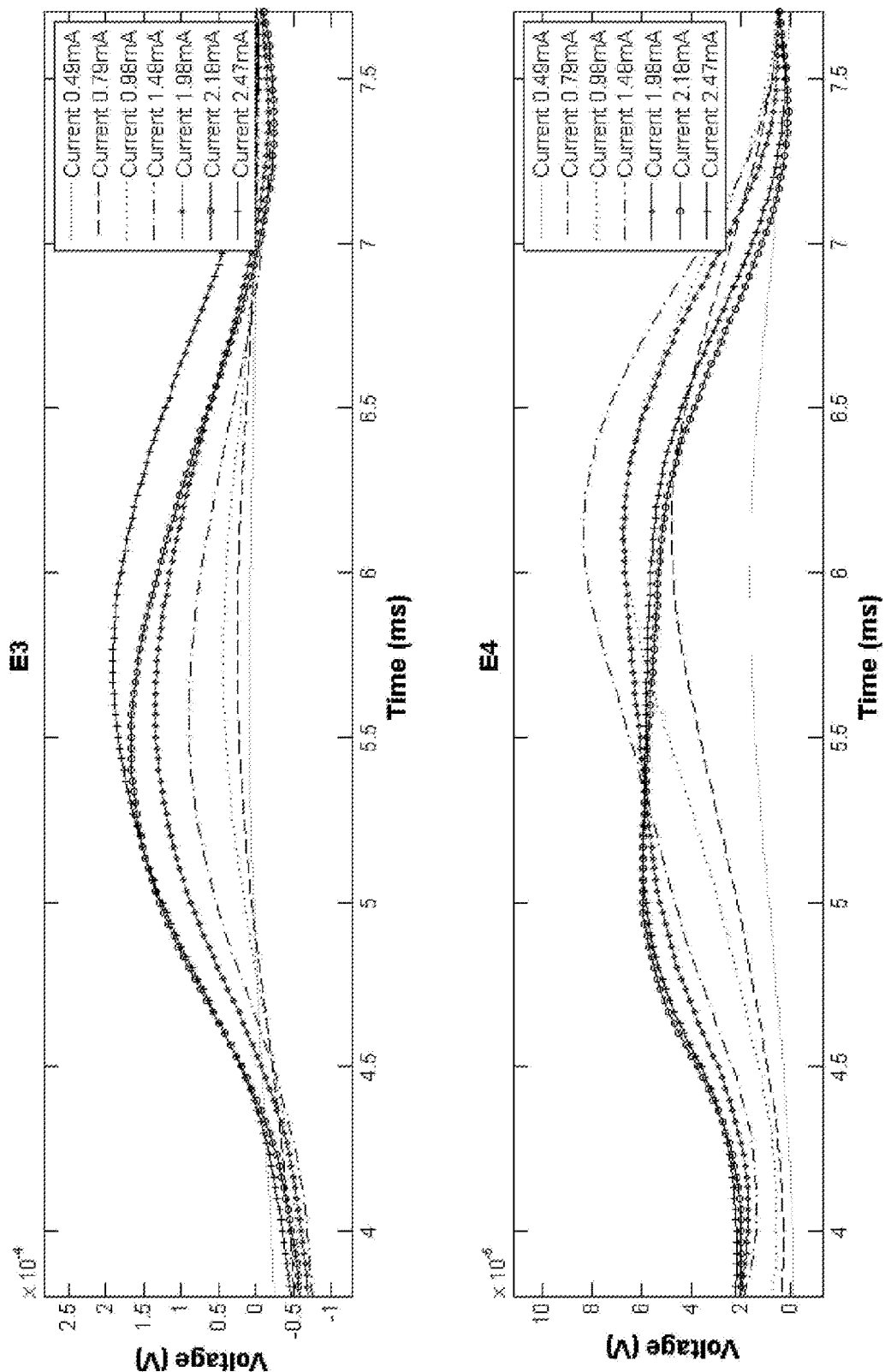
FIG. 18 illustrates late response measurements obtained in respect of another patient receiving STN DBS.

FIG. 18 illustrates late response measurements obtained in respect of yet another Parkinsons patient receiving STN DBS. Once again, a marked alteration occurs in the late response with increasing stimulus amplitude, however in this case the observed change is a reduction in latency of the late response, in contrast to the increased latency observed in FIGS. 4, 14b and 16b. However, once again, the point at which the change occurred (2 mA stimulus) corresponded to the point at which the therapy became effective for the patient, once again illustrating that a change in the late response is a useful biomarker. The change may be sought by monitoring latency of the late response, amplitude of the later response, or morphology of the late response such as the appearance of an additional peak in the late response as observed in FIG. 18, or the disappearance of a peak in the late response from the measurement window.

There are a vast number of other disease states which are treatable by DBS which include chronic depression, phantom pain, dependence, Huntington's disease, Tourette's syndrome and Alzheimer's disease. For all these disorders and for other applications, the combination of neuromodulation and drug administration may prove more effective than either alone. The majority of the CNS active pharmacological substances act on neural receptors or neurotransmitter release or metabolism. These in turn have an effect on the electrophysiology of the neurons which can be detected by measurement of ECAPs and/or late responses. The above methodology and techniques apply in all those cases and the concepts can be generalised to any type of neuromodulation in any brain centre.

Thus, while the present embodiments have been described in relation to measurement of a late response arising in response to stimulation of the subthalamic nucleus, it is to be appreciated that the present invention is also applicable in relation to the application of stimuli to other portions of the brain in which an early neural response arises in a linear manner in response to the stimulus, and in which a non-linear late response subsequently arises which may be separately monitored to the early response.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of monitoring neural activity in a brain arising from a stimulus, the method comprising:
   applying a plurality of stimuli to a target structure of the brain, where stimuli in the plurality of stimuli are delivered at varied amplitudes;
   obtaining a plurality of neural measurements from at least one electrode implanted in contact with the target structure, each neural measurement configured to capture a measure of any late response arising in the target structure resulting from a corresponding stimulus in the plurality of stimuli; and
   identifying a first and a second neural measurement in the plurality of neural measurements that describe a respective first and second late response, the respective first and second late responses being neural responses arising after an evoked compound action potential;
   identifying a therapeutic transition by identifying a temporal shift between the respective first and second late responses;
   defining a therapeutic stimulus amplitude based on a given amplitude of a stimulus corresponding to the second neural measurement, where the given amplitude is greater than an amplitude of a stimulus corresponding to the first neural measurement; and
   controlling a subsequent deep brain stimulation (DBS) therapy to mitigate the symptoms of a neurological condition, wherein the DBS therapy comprises applying a subsequent stimulus to the target structure, where the subsequent stimulus is delivered at the therapeutic stimulus amplitude in order to increase life of a battery used to apply the subsequent stimulus.

2. The method of claim 1 wherein the neural measurement encompasses a time period beginning in the range 1.5-4 ms after the stimulus onset.

3. The method of claim 2 wherein the plurality of neural measurements are obtained in a time period beginning 2-3 ms after the stimulus onset.

4. The method of claim 1 wherein the plurality of neural measurements are obtained in a time period ending in the range 5-10 ms after the stimulus onset.

5. The method of claim 4 wherein the plurality of neural measurements are obtained in a time period ending in the range 5.5-8 ms after the stimulus onset.

6. The method of claim 5 wherein the plurality of neural measurements are obtained in a time period ending in the range 6.5-7.5 ms after the stimulus onset.

7. The method of claim 1 wherein the target structure is the subthalamic nucleus.

8. The method of claim 1 wherein the plurality of neural measurements are obtained in a time period configured to also capture a measure of any compound action potential arising directly from the stimulus, prior to the late response.

9. The method of claim 1 further comprising, comparing a characteristic of the respective first late response to a healthy range in order to diagnose a disease state.

10. The method of claim 9 wherein the characteristic of the late response is one or more of the presence, amplitude, morphology, and latency of the late response.

11. The method of claim 1 further comprising, upon determining the presence of the respective first late response, monitoring a characteristic of subsequent late responses for changes over time, in order to diagnose a disease state.

12. The method of claim 1 wherein the DBS is to regulate neural activity to a target level or target profile.

13. The method of claim 1, further comprising adjusting a stimulation paradigm of the DBS.

14. The method of claim 1 further comprising monitoring the plurality of neural measurements to assess beta-band oscillations influencing the respective first and second neural late responses.

15. The method of claim 1, wherein the neurological condition is selected from the group consisting of: Parkinson's disease, Huntington's disease, Tourette's syndrome, chronic depression, dependence, tremor, Alzheimer's disease and dystonia.

16. The method of claim 1, wherein the temporal shift is at least 0.5 ms.

17. The method of claim 1, wherein the temporal shift is identified by reference to a temporal location of a peak in the respective first and second late response.

18. An implantable device for monitoring neural activity in the brain arising from a stimulus, the device comprising:
   a stimulus source powered by a battery for providing a plurality of stimuli to be delivered from one or more stimulus electrodes to a target structure of the brain, where stimuli in the plurality of stimuli are delivered at varied amplitudes;
   measurement circuitry for obtaining a plurality of neural measurements from a sense electrode in contact with the target structure, the neural measurement configured to capture a measure of any late response arising in the target structure resulting from a corresponding stimulus in the plurality of stimuli; and
   a processor configured to:
      identify a first and a second neural measurement in the plurality of neural measurements that describe a respective first and second late response, the respective first and second late responses being neural responses arising after an evoked compound action potential;
      identify a therapeutic transition by identifying a temporal shift between the respective first and second late responses;

define a therapeutic stimulus amplitude based on a given amplitude of a stimulus corresponding to the second neural measurement, where the given amplitude is greater than an amplitude of a stimulus corresponding to the first neural measurement; and control a subsequent deep brain stimulation (DBS) therapy to mitigate the symptoms of a neurological condition, wherein the DBS therapy comprises applying a subsequent stimulus to the target structure, where the subsequent stimulus is delivered at the therapeutic stimulus amplitude in order to increase life of the battery.

19. The system of claim 18, wherein the temporal shift is at least 0.5 ms.

20. A non-transitory computer readable medium for monitoring neural activity in the brain arising from a stimulus, comprising instructions which, when executed by one or more processors, causes performance of the following:

applying a plurality of stimuli to a target structure of the brain, where stimuli in the plurality of stimuli are delivered at varied amplitudes;

obtaining a plurality of neural measurements from at least one electrode implanted in contact with the target structure, each neural measurement configured to capture a measure of any late response arising in the target structure resulting from a corresponding stimulus in the plurality of stimuli; and identifying a first and a second neural measurement in the plurality of neural measurements that describe a respective first and second late response, the respective first and second late responses being neural responses arising after an evoked compound action potential;

identifying a therapeutic transition by identifying a temporal shift in between the respective first and second late responses;

defining a therapeutic stimulus amplitude based on a given amplitude of a stimulus corresponding to the second neural measurement, where the given amplitude is greater than an amplitude of a stimulus corresponding to the first neural measurement; and controlling a subsequent deep brain stimulation (DBS) therapy to mitigate the symptoms of a neurological condition, wherein the DBS therapy comprises applying a subsequent stimulus to the target structure, where the subsequent stimulus is delivered at the therapeutic stimulus amplitude in order to increase life of a battery used to apply the subsequent stimulus.

* * * * *